US006878518B2

(12) United States Patent
Whitehead

(10) Patent No.: US 6,878,518 B2
(45) Date of Patent: Apr. 12, 2005

(54) METHODS FOR DETERMINING STEROID RESPONSIVENESS

(75) Inventor: Alexander Steven Whitehead, Wayne, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 75 days.

(21) Appl. No.: 10/045,360

(22) Filed: Jan. 22, 2002

(65) Prior Publication Data

US 2003/0138781 A1 Jul. 24, 2003

(51) Int. Cl.[7] ............................ C12Q 1/68; C12P 19/34; C07H 21/02

(52) U.S. Cl. ........................ 435/6; 435/91.2; 536/23.1; 536/24.3

(58) Field of Search .................... 435/6, 91.2; 536/23.1, 536/24.3

(56) References Cited

U.S. PATENT DOCUMENTS

| | | | |
|---|---|---|---|
| 5,744,304 A | 4/1998 | Munford | 435/6 |
| 5,851,822 A | 12/1998 | Munford | 435/320.1 |
| 6,300,085 B1 * | 10/2001 | Alkon | 435/7.21 |

OTHER PUBLICATIONS

Chikanza et al, "The effects of hydrocortisone on in vitro lymphocyte proliferation and interleukin 2 and 4 production in corticosteroid sensitive and resistant subjects" (Eur. J. Clinical Investigation (1993) 23:845–850).*
Yap et al, "Th1 and Th2 cytokine mRNA profiles in childhood nephrotic syndrome: Evidence for increased IL–13 mRNA expression in relapse" (J. Am. Soc. Nephrol. (1999) 10:529–537).*
Baumann et al., "Interaction of Cytokine– and Glucocorticoid–Response Elements of Acute–Phase Plasma Protein Genes", The Journal of Biological Chemistry, vol. 265, No. 36, pp. 22275–22281, Dec. 25, 1990.
Nickerson et al., "Automated DNA Diagnostics Using an ELISA–Based Oligonucleotide Ligation Assay", Proc. Natl. Acad. Sci., vol. 87, pp. 8923–8927, Nov. 1990.
Scheidereit et al., "The glucocorticoid Receptor Binds to Defined Nucleotide Sequences Near the Promoter of Mouse Mammary Tumour Virus", Nature, vol. 304, pp. 749–752, Aug. 25, 1983.
Tobe et al., "Single–Well Genotyping of Dialletic Sequence Variations by a Two–Color ELISA–Based Oligonucleotide Ligation Assay", Nucleic Acids Research, vol. 24, No. 19, 1996.
Butler et al., "Structure of the Mouse Serum Amyloid A 5 (SAA5) Gene: Relationship to Other Members of the Serum Amyloid A Family", Scand. J. Immunol., vol. 45, pp. 160–165, 1997.

Butler et al., "Mapping of the Mouse Serum Amyloid A Gene Cluster by Long–Range Polymerase Chain Reaction", Immunogenetics, vol. 44, pp. 468–474, 1996.
Cohen et al., "Therapy of Relapsing Multiple Sclerosis. Treatment Approaches for Nonresponders", J. Neuroimmunol., vol. 98, pp. 29–36, 1999.
Cunnane et al., "Amyloid Precursors and Amyloidosis in Rheumatoid Arthritis", Bailliére's Clinical Rheumatol., vol. 13, No. 4, pp. 615–628, 1999.
Cunnane et al., "Serum Amyloid A in the Assessment of Early Inflammatory Arthritis", Rheumatol., 27:1, 2000.
Gaughan et al., "Ribozyme Mediated Cleavage of Acute Phase Serum Amyloid A (A–SAA) mRNA in Vitro", FEBS Letters, 374, pp. 241–245, 1995.
Gaughan et al., "Efficient In Vitro Cleavage of Mouse Acute Phase Serum Amyloid A mRNA Mediated by a Synthetic Hammerhead Ribozyme", Scand. J. Immunol., vol. 46, pp. 51–58, 1997.
Grehan et al., "Expression of a Biologically Active Recombinant Mouse IL–1 Receptor Antagonist and its Use in Vivo to Moduate Aspects of the Acute Phase Response", J. Immunol., pp. 369–378, 1997.
Grehan et al., "Down–Regulation of the Major Circulating Precursors of Proteins Deposited in Secondary Amyloidosis by a Recombinant Mouse Interleukin–1 Receptor Antagonist", Eur. J. Immunol., vol. 27, pp. 2593–2599, 1997.
Hanauer et al., "Management of Crohn's Disease in Adults", Amer. J. Gastroenter., vol. 92, No. 4, 1997.
Hendrickse et al., "Rifampicin–Induced Non–Responsiveness to Corticosteroid Treatment in Nephrotic Syndrome", Brit. Med. J., p. 306, Feb. 3, 1979.
Jain et al., "Rifampicin Induced Non–Responsiveness to Steroids in Bronchial Asthma", Indian. J. Chest. Dis. & All Sci., vol. 31, No. 4, pp. 271–274, 1989.
Jensen et al., "Competitive Reverse Transcription Polymerase Chain Reaction for Quantifying Pre–mRNA and mRNA of Major Acute Phase Proteins", J. Immunol. Meth., vol. 215, pp. 45–48, 1998.
Jensen et al., "Review Article—Regulation of Serum Amyloid a Protein Expression During the Acute–Phase Response", Biochem. J., vol. 334, pp. 489–503, 1998.

(Continued)

*Primary Examiner*—Jeffrey Fredman
(74) *Attorney, Agent, or Firm*—Morgan, Lewis & Bockius, LLP

(57) ABSTRACT

The invention provides a diagnostics assay for measuring the responsiveness to a drug by comparing the mRNA levels of a gene that responds to the drug, such as a steroid, to the mRNA levels of a gene that does not respond to the drug. Methods according to the invention are useful for predicting the ability of a patient (or a tissue, body fluid or cell sample in vitro) to respond to a drug or steroid at any stage of their treatment (i.e., before, during or after), and to monitor the patient (or a tissue, body fluid or cell) over time to assess continued responsiveness to the drug or steroid.

60 Claims, 8 Drawing Sheets

OTHER PUBLICATIONS

Jensen et al., "Evolutionary Analyses and Acute Phase Response", J. Imunol., pp. 384–392, 1997.

Jorgensen et al., "Serum Amyloid A Transcription in Atlantic Salmon (*Salmo salar L.*) Hepatocytes is enhanced by Stimulation with Macrophage Factors, Recombinant Human IL–1β, IL–6 and TNFα or bacterial lipopolysaccharide", Devel. and Compar. Immunol., vol. 24, pp. 553–563, 2000.

Kornbluth et al., "Ulcerative Colitis Practice Guidelines in Adults", Am. J. of Gastroent., vol. 92, No. 2, 1997.

Longley et al., "Posttranscriptional Regulation of Acute Phase Serum Amyloid A2 Expression by the 5'-and 3'—Untranslated Regions of Its mRNA", J. Immunol., pp. 4538–4545, 1999.

McCormack et al., "Generation of Soluble Recombinant Human Acute Phase Serum Amyloid A2 (A–SAA2) Protein and its Use in Development of a A–SAA Specific ELISA", J. Immunol. Meth., vol. 198, pp. 101–110, 1996.

O'Hara et al., "Acute–Phase Serum Amyloid A Production by Rheumatoid Arthritis Synovial Tissue", Arthritis Res. vol. 2, pp. 142–144, 2000.

O'Mahony et al., "Review Article: Management of Patients with Non–Responsive Cocliac Disease", Aliment Pharmacol. Ther., vol. 10, pp. 671–68, 1996.

Present, "How To Do Without Steriods in Inflammatory Bowel Disease", Inflamm. Bowel Dis., vol. 6, No. 1, Feb. 2000.

Rebuck, "Asthma: Non–Responsiveness to Conventional Therapy", Eur. J. Respir. Dis., 69 (Suppl. 147), pp. 105–109, 1986.

Rygg et al., "In Vitro Evaluation of an Enhanced Human Serum Amyloid A (SAA2) Promoter–Regulated Soluble TNF Receptor Fusion Protein for Anti–Inflammatory Gene Therapy", Scand. J. Immunol., vol. 53, pp. 588–595, 2001.

Spitz et al., "Response to the Antiprogestagen RU 486 (mifepristone) During Early Pregnancy and the Menstrual Cycle in Women", J. Reprod. Fert., Suppl., vol. 37, pp. 253–260, 1989.

Steel et al., "Expression and Regulation of Constitutive and Acute Phase Serum Amyloid A mRNAs in Hepatic and Non–Hepatic Cell Lines", Scand. J. Immunol., vol. 44, pp. 493–500, 1996.

Uhlar et al., "Wallaby Serum Amyloid A Protein: cDNA Cloning, Sequence and Evolutionary Analysis", Scand. J. Immunol., vol. 43, pp. 271–276, 1996.

Uhlar et al., "The Kinetics and Magnitude of the Synergistic Activation of the Serum Amyloid A Promoter by IL–1 β and IL–6 is Determined by the Order of Cytokine Addition", Scand. J. Immunol., vol. 49, pp. 399–404, 1999.

Uhlar et al., "Use of the Acute Phase Serum Amyloid A2 (SAA2) Gene Promoter in the Analysis of Pro– and Anti––Inflammatory Mediators: Differential Kinetics of SAA2 Promoter Induction by IL–1 β and TNF–α compared to IL–6", J. Immunol. Meth., vol. 203, pp. 123–130, 1997.

Uhlar et al., "Review Article—Serum Amyloid A, the Major Vertebrate Acute–Phase Reactant", Eur. J. Biochem., vol. 265, pp. 501–523, 1999.

* cited by examiner

```
              YY-1                           AP-1
SAA1  --TAGATATG AACTCAGAGG GACTTCATTT CAGAGGCATC TGCCATGTGG⁻³⁹¹
SAA2  TTTAGACATG AACTCACAGG GATTTCAGT- CAGGGTCATC TGCCATGTGG₋₃₉₇
      ****  ***  ****** ***  ** **** *  *** * **** **********
      AP-2                    NF-IL-6/YY-1
SAA1  CCCAGCAGAG CCCATCCTGA GGAAATGACT GGTAGAGTCA GGAGCTGGCT⁻³⁴¹
SAA2  CCCAGCAGGG CCCATCCTGA GGAAATGACC GGTATAGTCA GGAGCTGGCT₋₃₄₇
      *******  *  **********  ********  ****  *****  **********
                                                         YY-1
SAA1  TCAAAGCTGC CCTCACTTCA CACCTTCCAG CAGCCCAGGT GCCGCCATCA⁻²⁹¹
SAA2  GAAGAGCTGC CCTCACTCCA CACCTTCCAG CAGCCCAGGT GCCGCCATCA₋₂₉₇
      * ******  *******  **  **********  **********  **********
      NFκB                            AP-2  SAE
SAA1  CGGGGCTCCC ACTCTCAACT CCGCAGCCTC AGCCCCCTCA ATGCTGAGGA⁻²⁴¹
SAA2  CGGGGCTCCC ACTGGCATCT CTGCAGCTGC ACTTCCCCCA ATGCTGAGGA₋₂₄₇
      **********  ***  ** **  * *****  * *  *** **  **********
      -240
SAA1  GCAGAGCTGG TCTCCTGCCC TGACAGCTGC CA-GGCACA- --------TC⁻²⁰¹
SAA2  GCAGAGCTGA TCTAGCACCC TGTCCATTGC CAAGGCACAG CAAACCTCTC₋₁₉₇
      ********  ***    ***  ** *  ***  ** ******           **
      -200 GRE         NF-IL6/STAT           AP-1......
SAA1  TTGTTCCCTC AGGTTGCACA ACTGGGATAA ATGACCCGGG ATGAAGAAAC⁻¹⁵¹
SAA2  TTGTTCCCAT AGGTTACACA ACTGGGATAA ATGACCCGGG ATGAAGAAAC₋₁₄₇
      ********   *****  ****  **********  *********  **********
      -150                                         YY-1
SAA1  CACTGGCATC CAGGAACTTG TCTTAGACCG TTTGTAGGG GAAATGACCT⁻¹⁰¹
SAA2  CACCGGCATC CAGGAACTTG TCTTAGACCA GTTGTAGGG GAAATGACCT₋₉₇
      ***  ******  **********  ********   ********  **********
      -100 NFκB
SAA1  GCAGGGACTT TCCCCAGGGA CCACATCCAG CTTTTCTTCC CTCCCAAGAA⁻⁵¹
SAA2  GCAGGGACTT TCCCCAGGGA CCACATCCAG CTTTTCTTCC CTCCCAAGAG₋₄₇
      **********  **********  **********  **********  *********
      -50      SP-1
SAA1  ACCAGCAGGG AAGGCTCAGT ATAAATAGCA GCCACCGCTC CCTGGCAGGC⁻¹
SAA2  ACCAGCA--- -AGGCTCACT ATAAATAGCA GCCACCTCTC CCTGGCAGAC₋₁
      *******       ****** *  **********  ******  *** *******  *
```

FIG. 1

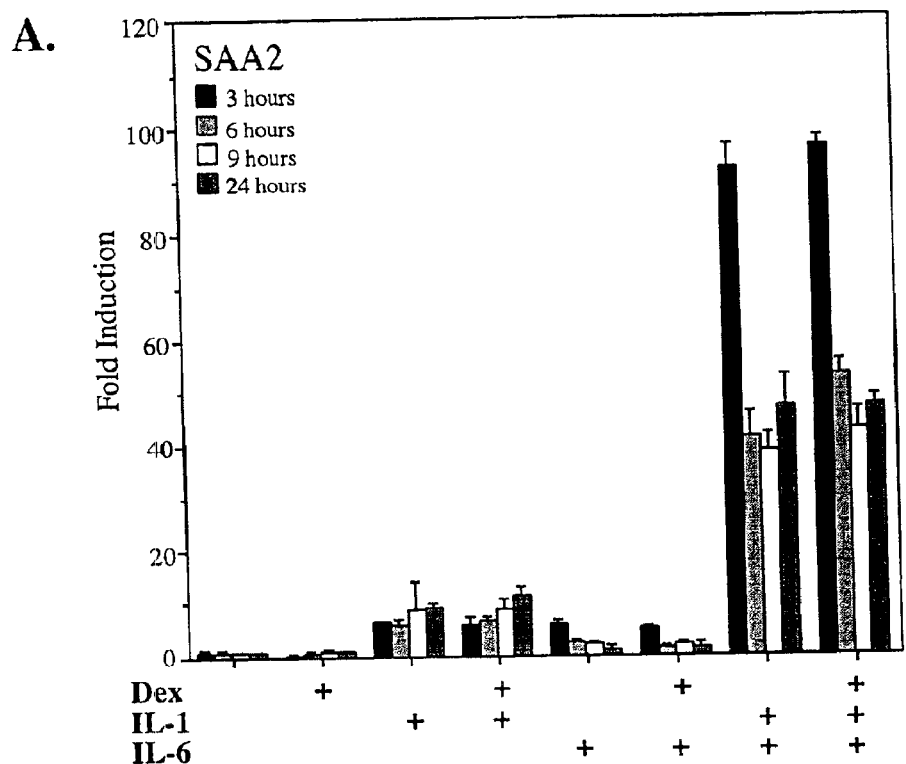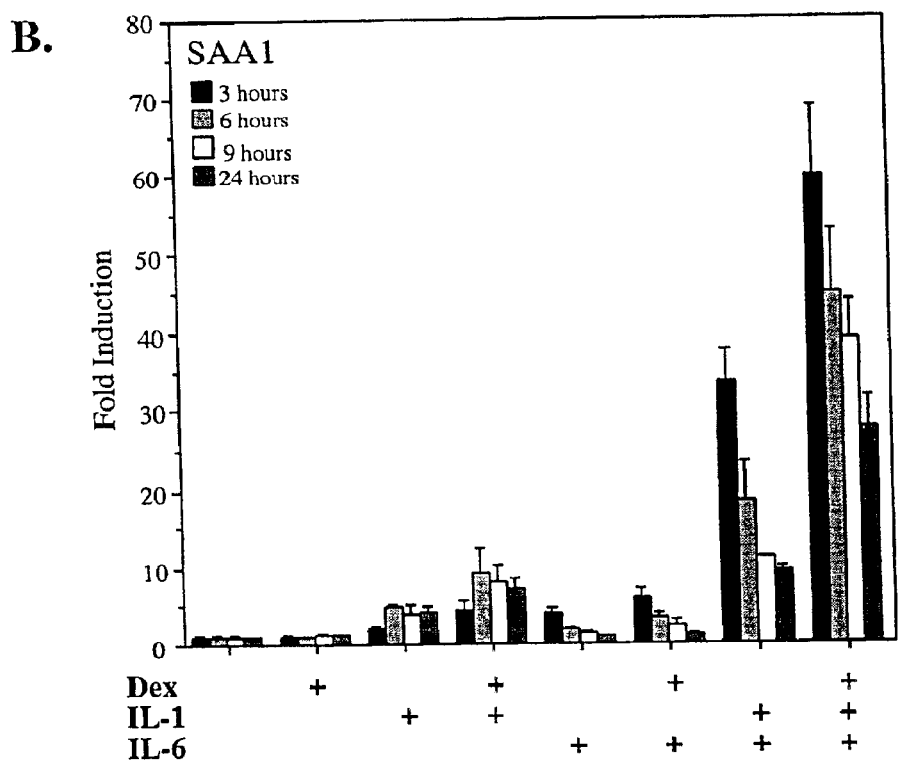
FIG. 2

A.

```
SAA1  CAGACAAATACTTCCATGCTCGGGGGAACTATGATGCTGCCAAAAGGGGACCTGGGGGTG246
SAA2  CAGACAAATACTTCCATGCTCGGGGGAACTATGATGCTGCCAAAAGGGGACCTGGGGGTG246
                    exon3   exon4
SAA1  TCTGGGCTGCAGAAGCGATCAG|CGATG—//—//—TGAGCTTCCTCTTCACTCTGCTC426
SAA2  CCTGGGCCGCAGAAGTGATCAG|CAATG—//—//—TGAGCTTCCTCTTCACTCTGCTC426

SAA1  TCAGGAGATCTGGCTGTGAGGC-TCAGGGCAGGGATACAAAGC----GGGG--------472
SAA2  TCAGGAGACCTGGCTATGAGCCCTCGGGGCAGGGATTCAAAGTTAGTGAGGTCTATGTCC486

SAA1  AGAG-----------GGTACACAATGGGTATCTAATAAATACTTAAGAGGTGGAAAAAA520
SAA2  AGAGAAGCTGAGATATGGCATATAATAGGCATCTAATAAATGCTTAAGAGGTGGAAAAAA546
```

B.

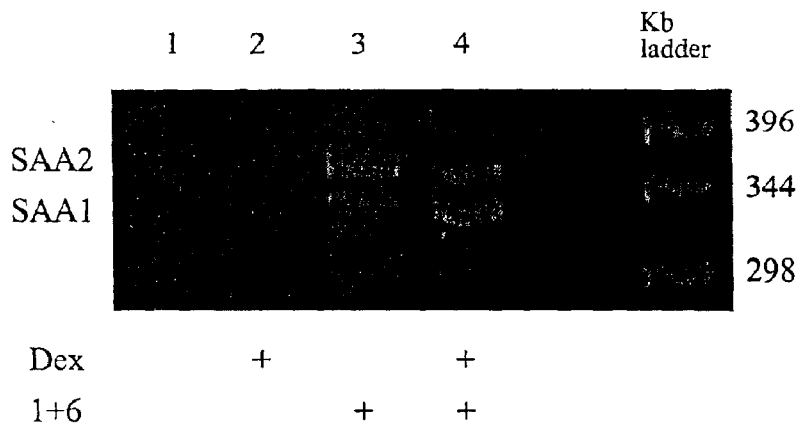

```
            1    2    3    4    Kb
                                ladder
SAA2                            396
SAA1                            344
                                298

Dex          +         +
1+6               +    +
```

FIG. 8

SEQUENCE LISTING

<160> NUMBER OF SEQ ID NOS: 23

<210> SEQ ID NO 1
<211> LENGTH: 15
<212> TYPE: DNA
<213> ORGANISM: Artificial Sequence
<220> FEATURE:
<223> OTHER INFORMATION: Glucocorticoid Responsive Element GRE consensus
      sequence
<221> NAME/KEY: n
<222> LOCATION: (7)..(9)
<223> OTHER INFORMATION: any nucleotide (A, G, C or T)

<400> SEQUENCE: 1
ggtacannnt gttct                                                    15

<210> SEQ ID NO 2
<211> LENGTH: 438
<212> TYPE: DNA
<213> ORGANISM: Homo sapiens

```
<400> SEQUENCE: 2
tagatatgaa ctcagaggga cttcatttca gaggcatctg ccatgtggcc cagcagagcc      60
catcctgagg aaatgactgg tagagtcagg agctggcttc aaagctgccc tcacttcaca     120
ccttccagca gcccaggtgc cgccatcacg gggctcccac tctcaactcc gcagcctcag     180 cccccctcaat gctgaggagc agagctggtc tcctgccctg acagctgcca ggcacatctt    240
gttccctcag gttgcacaac tgggataaat gacccgggat gaagaaacca ctggcatcca     300
ggaacttgtc ttagaccgtt ttgtagggga aatgacctgc agggactttc cccagggacc     360
acatccagct tttcttccct cccaagaaac cagcagggaa ggctcagtat aaatagcagc     420
caccgctccc tggcaggc                                                   438

<210> SEQ ID NO 3
<211> LENGTH: 445
<212> TYPE: DNA
<213> ORGANISM: Homo sapiens

<400> SEQUENCE: 3
tttagacatg aactcacagg gatttcagtc agggtcatct gccatgtggc ccagcagggc     60
ccatcctgag gaaatgaccg gtatagtcag gagctggctg aagagctgcc ctcactccac    120
accttccagc agcccaggtg ccgccatcac ggggctccca ctggcatctc tgcagctgca    180
cttcccccaa tgctgaggag cagagctgat ctagcaccct gtccattgcc aaggcacagc    240
aaacctctct tgttcccata ggttacacaa ctgggataaa tgacccggga tgaagaaacc    300
accggcatcc aggaacttgt cttagaccag tttgtagggg aaatgacctg cagggacttt    360
ccccagggac cacatccagc ttttcttccc tcccaagaga ccagcaaggc tcactataaa    420
tagcagccac ctctccctgg cagac                                          445

<210> SEQ ID NO 4
<211> LENGTH: 87
<212> TYPE: DNA
<213> ORGANISM: Homo sapiens

<400> SEQUENCE: 4
cagacaaata cttccatgct cgggggaact atgatgctgc caaaagggga cctgggggtg     60
tctgggctgc agaagcgatc agcgatg                                        87

<210> SEQ ID NO 5
<211> LENGTH: 117
<212> TYPE: DNA
<213> ORGANISM: Homo sapiens

<400> SEQUENCE: 5
tgagcttcct cttcactctg ctctcaggag atctggctgt gaggctcagg gcagggatac     60
aaagcgggga gagggtacac aatgggtatc taataaatac ttaagaggtg gaaaaaa       117

<210> SEQ ID NO 6
<211> LENGTH: 87
<212> TYPE: DNA
<213> ORGANISM: Homo sapiens

<400> SEQUENCE: 6
cagacaaata cttccatgct cgggggaact atgatgctgc caaaagggga cctgggggtg     60
cctgggccgc agaagtgatc agcaatg                                        87
```

<210> SEQ ID NO 7
<211> LENGTH: 143
<212> TYPE: DNA
<213> ORGANISM: Homo sapiens

<400> SEQUENCE: 7

```
tgagcttcct cttcactctg ctctcaggag acctggctat gagccctcgg ggcagggatt      60
caaagttagt gaggtctatg tccagagaag ctgagatatg gcatataata ggcatctaat     120
aaatgcttaa gaggtggaaa aaa                                             143
```

<210> SEQ ID NO 8
<211> LENGTH: 53
<212> TYPE: DNA
<213> ORGANISM: Artificial Sequence
<220> FEATURE:
<223> OTHER INFORMATION: PCR primer specific for human SAA2 gene

<400> SEQUENCE: 8

```
aagaattcac gcgtccatgc atgttgcggc cgcttggcca tcctttactt cct             53
```

<210> SEQ ID NO 9
<211> LENGTH: 49
<212> TYPE: DNA
<213> ORGANISM: Artificial Sequence
<220> FEATURE:
<223> OTHER INFORMATION: PCR probe specific for human SAA2 gene

<400> SEQUENCE: 9

```
ttgaattcct cgagcaggta ccatacatat gtagctgagc tgcgggtcc                  49
```

<210> SEQ ID NO 10
<211> LENGTH: 42
<212> TYPE: DNA
<213> ORGANISM: Artificial Sequence
<220> FEATURE:
<223> OTHER INFORMATION: Forward PCR primer for human SAA1 gene

<400> SEQUENCE: 10

```
gaattcacgc gtttgggcag ggaatatact tatttatgga ag                         42
```

<210> SEQ ID NO 11
<211> LENGTH: 42
<212> TYPE: DNA
<213> ORGANISM: Artificial Sequence
<220> FEATURE:
<223> OTHER INFORMATION: Reverse PCR primer for human SAA1 gene

<400> SEQUENCE: 11

```
gaattcccat ggtgctgatc tgtgctgtag ctgagctgcg gg                         42
```

<210> SEQ ID NO 12
<211> LENGTH: 42
<212> TYPE: DNA
<213> ORGANISM: Artificial Sequence
<220> FEATURE:
<223> OTHER INFORMATION: Forward PCR primer for human SAA1 gene

<400> SEQUENCE: 12

```
gaattcacgc gtgcgtgatt atagctcact gcagccttga cc                         42
```

<210> SEQ ID NO 13
<211> LENGTH: 25
<212> TYPE: DNA
<213> ORGANISM: Artificial Sequence

```
<220> FEATURE:
<223> OTHER INFORMATION: Forward PCR primer for human SAA1 gene

<400> SEQUENCE: 13
gaattcacgc gtggtctcct gcctg                                     25

<210> SEQ ID NO 14
<211> LENGTH: 32
<212> TYPE: DNA
<213> ORGANISM: Artificial Sequence
<220> FEATURE:
<223> OTHER INFORMATION: Forward PCR primer for human SAA2 gene

<400> SEQUENCE: 14
tataacgcgt cctatttaac gcaccacact ct                             32

<210> SEQ ID NO 15
<211> LENGTH: 25
<212> TYPE: DNA
<213> ORGANISM: Artificial Sequence
<220> FEATURE:
<223> OTHER INFORMATION: Forward PCR primer for human SAA2 gene

<400> SEQUENCE: 15
gaattcacgc gtgatctagc acctg                                     25

<210> SEQ ID NO 16
<211> LENGTH: 20
<212> TYPE: DNA
<213> ORGANISM: Artificial Sequence
<220> FEATURE:
<223> OTHER INFORMATION: PCR mutagenesis primer GREIF

<400> SEQUENCE: 16
cagcaaacct ctcttgtccc                                           20

<210> SEQ ID NO 17
<211> LENGTH: 19
<212> TYPE: DNA
<213> ORGANISM: Artificial Sequence
<220> FEATURE:
<223> OTHER INFORMATION: PCR mutagenesis primer GREIR

<400> SEQUENCE: 17
agagaggttt gctgtgcct                                            19

<210> SEQ ID NO 18
<211> LENGTH: 25
<212> TYPE: DNA
<213> ORGANISM: Artificial Sequence
<220> FEATURE:
<223> OTHER INFORMATION: PCR mutagenesis primer GREDF

<400> SEQUENCE: 18
caaggcacat cttgttccca taggt                                     25

<210> SEQ ID NO 19
<211> LENGTH: 24
<212> TYPE: DNA
<213> ORGANISM: Artificial Sequence
<220> FEATURE:
<223> OTHER INFORMATION: PCR mutagenesis primer GREDR

<400> SEQUENCE: 19
ggaacaagat gtgccttggc aatg                                      24
```

```
<210> SEQ ID NO 20
<211> LENGTH: 20
<212> TYPE: DNA
<213> ORGANISM: Artificial Sequence
<220> FEATURE:
<223> OTHER INFORMATION: RT-PCR forward primer

<400> SEQUENCE: 20
cagacaaata cttccatgct                                               20

<210> SEQ ID NO 21
<211> LENGTH: 29
<212> TYPE: DNA
<213> ORGANISM: Artificial Sequence
<220> FEATURE:
<223> OTHER INFORMATION: Reverse RT-PCR primer

<400> SEQUENCE: 21 tttttccac ctcttaagta tttattaga                                      29

<210> SEQ ID NO 22
<211> LENGTH: 29
<212> TYPE: DNA
<213> ORGANISM: Artificial Sequence
<220> FEATURE:
<223> OTHER INFORMATION: Reverse RT-PCR primer

<400> SEQUENCE: 22 tttttccac ctcttaagca tttattaga                                      29

<210> SEQ ID NO 23
<211> LENGTH: 15
<212> TYPE: DNA
<213> ORGANISM: Homo sapiens

<400> SEQUENCE: 23
ggcacatctt gttcc                                                    15
```

METHODS FOR DETERMINING STEROID RESPONSIVENESS

FIELD OF THE INVENTION

The invention relates to a diagnostic assay for steroid responsiveness.

BACKGROUND OF THE INVENTION

Many diseases (e.g., rheumatoid arthritis, inflammatory bowel diseases, systemic lupus erythematosis, asthma) that are primarily inflammatory, or that have a major inflammatory component, are treated with steroids such as prednisone. In addition, some cancers are treated with steroids, as are transplant recipients, to avoid transplant rejection. However, the effectiveness of steroids varies from patient to patient and is usually impossible to predict. Some patients may be constitutively non-responsive to a particular medication, and others may become refractory to treatment over time. In some cases, patients may experience symptomatic relief, but attempts to withdraw therapy lead to disease flare. As a consequence, the inclination for doctors to continue steroid therapy and even to increase the dosage of a steroid is associated with serious, cumulatively debilitating, side effects. The clinical screening of patients who are candidates for steroid therapy for their ability to respond to steroids and the monitoring of patients who are undergoing steroid therapy but who may be transitioning from steroid responder to non-responder (i.e., refractory) status is therefore of significant clinical importance.

A need therefore exists for a diagnostic assay or test for steroid responsiveness.

SUMMARY OF THE INVENTION

The invention provides diagnostic assays for measuring the response to a drug by comparing mRNA levels expressed by a gene that is expected to respond to the drug to mRNA levels expressed by a gene that is not expected to respond to the drug. The invention is based on observations that expression in drug-sensitive genes is useful as a marker for the cellular response to the drug. Methods according to the invention are useful for predicting the ability of a patient (or a tissue, body fluid or cell sample in vitro) to respond to a treatment before treatment begins and to monitor treatment over time to assess continued responsiveness to therapeutic intervention.

In one aspect, the invention provides methods for determining steroid responsiveness in a subject, by determining the level of expression of RNA from a first gene known or suspected to be steroid responsive, determining the level of expression of RNA from a second gene known or suspected to be non-responsive to steroids, and comparing them pre- and post-treatment to determine whether the subject is likely to respond to steroid treatment. The subject is determined to be steroid responsive if the level of expression from the first gene is higher than that from the second gene and the subject is non-responsive to steroids if the level of expression from the second gene is higher than that from the first gene. Alternatively, the ratio of the expression from the first gene to the expression from the second gene is compared to predetermined control ratios from untreated subjects or to predetermined control ratios from subjects undergoing successful treatment. For example, a subject may be steroid responsive if the ratio of the expression from the steroid responsive gene to the expression of the steroid non-responsive gene is similar to prior ratios for the subject when previously responsive or higher than the predetermined control ratio for untreated subjects or similar to predetermined control ratios from subjects undergoing successful treatment. Conversely, the subject may be steroid non-responsive if the ratio of the expression from the steroid responsive gene to the expression of the steroid non-responsive gene is lower than prior ratios for the subject when previously responsive or similar to the predetermined control ratio for untreated subjects or lower than predetermined control ratios from subjects undergoing successful treatment.

In another embodiment, the invention provides methods for determining steroid responsiveness in a tissue, body fluid or cell after exposure in vitro to a steroid.

In another embodiment, the invention provides methods for determining or predicting steroid responsiveness in a subject before and after (i.e., following or during administration of) steroid treatment. Samples are taken before and after steroid treatment, and the RNA levels for the steroid non-responsive gene are used as a normalizing control for the RNA levels of the steroid responsive gene. The invention provides for obtaining a pre-treatment tissue, body fluid or cell from a subject, determining the level of RNA expression from steroid responsive and steroid non-responsive genes, administering a steroid to the subject, obtaining a post-treatment tissue, body fluid or cell from the subject and determining a post-treatment RNA level expressed from the same genes identified in the pre-treatment samples, comparing the pre-treatment level of RNA expressed from the first gene to the pre-treatment level of RNA expressed from the second gene to create a first normalized value, comparing the post-treatment level of RNA expressed from the first gene to the post-treatment level of RNA expressed from the second gene to create a second normalized value, and comparing the first normalized value to the second normalized value. If the first normalized value is less than the second normalized value, the tissue, body fluid or cell sample is determined to be steroid responsive and if the first normalized value is greater than or the same as the second normalized value the tissue, body fluid or cell sample is determined to be steroid non-responsive. The difference between the first normalized value and the second normalized value correlates to the ability of the subject to respond to steroid treatment.

In another embodiment, the invention provides methods for determining an effective dose of a steroid in a subject by administering to a subject a dose of a steroid, obtaining a tissue, body fluid or cell sample from the subject, determining the level of expression of RNA from a first gene known or suspected to be steroid responsive, determining the level of expression of RNA from a second gene known or suspected to be non-responsive to steroids, and comparing them pre- and post-treatment to determine whether the dose of steroid is appropriate. Alternatively, the ratio of the expression from the first gene to the expression from the second gene is compared to predetermined control ratios from untreated subjects. This alternative allows for the continued assessment of effective dosage during a course of treatment if no pre-treatment sample is available, e.g., in the case of a chronic condition. For example, a subject may be receiving an adequate dosage of steroid if the ratio of the expression from the first gene to the expression from the second gene is higher than the predetermined control ratio for untreated subjects. The dosage may be titrated or lowered until just before the ratio of RNA levels from the steroid responsive to steroid non-responsive gene begins to decrease, in order to determine the minimum dosage that can be given to achieve optimal results. Alternatively, a subject may be given an initial low dose of steroid, the ratio of RNA levels from the steroid responsive to steroid non-responsive gene measured, and the dosage increased until the ratio reaches a plateau, or until the ratio reaches a desired target level.

In some cases a patient may be obtaining clinical benefit (e.g., symptomatic relief) from steroid therapy to later become refractory (i.e., non-responsive to the therapy). The instant invention provides methods for ensuring the long-term appropriateness and efficacy of a steroid treatment by monitoring a subject's ability to respond to the steroid. The invention provides methods for monitoring a subject's ability to respond to a steroid by administering to a subject a dose of steroid, obtaining a tissue, body fluid or cell sample from the subject, determining the level of expression of RNA from a first gene known or suspected to be steroid responsive, determining the level of expression of RNA from a second gene known or suspected to be non-responsive to steroids, and comparing them pre- and post-treatment to determine whether the subject is still responsive to steroid treatment. The subject is still steroid responsive if the level of expression from the steroid responsive gene is higher than that of the steroid non-responsive gene and the subject has become non-responsive to steroids if the level of expression from the steroid non-responsive gene is higher than that of the steroid responsive gene. Alternatively, the ratio of the expression from the steroid responsive gene to the expression from the steroid non-responsive gene is compared to predetermined control ratios from untreated subjects or to predetermined control ratios from subjects undergoing successful treatment or to a preexisting ratio from the subject obtained at a time when the subject was classified as steroid responsive. For example, a subject may be steroid responsive if the ratio of the expression from the steroid responsive gene to the expression of the steroid non-responsive gene is similar to prior ratios for the subject when previously responsive or higher than the predetermined control ratio for untreated subjects or similar to predetermined control ratios from subjects undergoing successful treatment. Conversely, the subject may be steroid non-responsive if the ratio of the expression from the steroid responsive gene to the expression of the steroid non-responsive gene is lower than prior ratios for the subject when previously responsive or similar to the predetermined control ratio for untreated subjects or lower than predetermined control ratios from subjects undergoing successful treatment.

More generally, the invention also provides a general approach to determining drug responsiveness generally in a subject undergoing drug treatment. In this method a first gene must be identified which responds to the drug by causing a change in RNA production (e.g., change in transcription, RNA stability, or RNA accumulation). A second gene must also be identified which does not respond to the drug by causing a change in RNA production. In another aspect, the invention provides methods for determining drug responsiveness in a subject undergoing drug treatment by determining the level of expression of RNA from a first gene known or suspected to be drug-responsive, determining the level of expression of RNA from a second gene known or suspected to be non-responsive to the drug, and comparing them pre- and post-treatment to determine whether the subject is likely to respond to drug treatment. The subject is determined to be drug-responsive if the level of expression from the drug-responsive gene is higher than that of the drug non-responsive gene and the subject is non-responsive to the drug if the level of expression from the drug non-responsive gene is higher than that of the drug-responsive gene. Alternatively, the ratio of the expression from the drug-responsive gene to the expression from the drug non-responsive gene is compared to predetermined control ratios from untreated subjects or to predetermined control ratios from subjects undergoing successful treatment. For example, a subject may be drug-responsive if the ratio of the expression from the drug-responsive gene to the expression of the drug non-responsive gene is similar to prior ratios for the subject when previously responsive or higher than the predetermined control ratio for untreated subjects or similar to predetermined control ratios from subjects undergoing successful treatment. Conversely, the subject may be drug non-responsive if the ratio of the expression from the drug-responsive gene to the expression of the drug non-responsive gene is lower than prior ratios for the subject when previously responsive or similar to the predetermined control ratio for untreated subjects or lower than predetermined control ratios from subjects undergoing successful treatment.

In another embodiment, the invention provides methods for determining drug responsiveness in a tissue, body fluid or cell after exposure in vitro to a drug.

In another embodiment, the invention provides methods for determining responsiveness in a tissue, body fluid or cell sample to a drug or drug candidate for determining alterations in the cellular response to pro-inflammatory, anti-inflammatory or immune response-modifying stimuli (e.g., cytokines, chemokines, steroids, etc.). In other words, the methods according to the invention may detect side effects of drugs on immune responses in cells. The cellular response may be assessed by comparing the relative levels of endogenous steroid responsive gene and steroid nonresponsive gene mRNA, as described herein. Alternatively, cells may be transfected with a vector or vectors having the steroid responsive gene and steroid nonresponsive gene promoters, each in operative linkage with a different detectable reporter gene (e.g., green fluorescence protein or yellow fluorescence protein). The method includes exposing the cell, transfected with the vector(s) having the steroid responsive gene and steroid nonresponsive gene promoter-driven reporter genes, to a drug of interest and comparing the level of expression from the first reporter gene to the level of expression from the second reporter gene. In this way, a drug that may or may not have pro- or anti-inflammatory or immune response-modifying activity can be assayed for its effect on gene expression from the steroid responsive gene and steroid nonresponsive gene promoters.

In a preferred embodiment, RNA levels are quantified by amplification of the RNA by, for example, reverse transcription polymerase chain reaction (RT-PCR) of the RNAs. The reaction products may be quantified, e.g., by gel electrophoresis (e.g., slab or cappillary) or the unamplified RNA may be quantified, e.g., by Northern blot analysis, or by direct hybridization with a probe. Alternatively, RNA levels are quantified by in situ detection. Diagnostic procedures may also be performed in situ directly upon sections (fixed or frozen) of tissue obtained from biopsies or resections by looking at relative intensities of drug or steroid responsive and drug or steroid nonresponsive RNAs in a portion of the biopsy sample, such that no nucleic acid purification is necessary. Nucleic acid reagents may be used as probes and/or primers for such in situ procedures.

RNA may be quantified from any tissue, body fluid or nucleated cell sample. For example, the tissue or body fluid sample is preferably blood. The tissue sample may be derived from a biopsy of any tissue in which the genes of interest (i.e., the drug or steroid responsive gene and the drug or steroid non-responsive gene) are expressed. The tissue, body fluid or cell sample may contain one or more of monocytes, macrophages, neutrophils, T-cells, B-cells, basophils, fibroblasts, smooth muscle cells, endothelial cells and epithelial cells, for example. In addition, the tissue or cell sample may be a benign tumor, malignant tumor, a tissue that is normally responsive to steroids (such as a breast cancer biopsy sample, e.g., to determine whether it has lost the ability to respond to steroids, has become less responsive to steroids, or has become more responsive to steroids) or a tissue that is non-responsive to steroids (e.g., to determine if it has gained responsiveness to steroids). In a preferred embodiment, the tissue used to measure RNA levels of the genes of interest contains buccal cells. The tissue, body fluid or cell sample is obtained and is preferably stored in a stabilization solution or is stored frozen prior to analysis to minimize RNA degradation.

In another embodiment of the invention, the methods involve the step of administering one or more pro-inflammatory or anti-inflammatory mediators to the tissue, body fluid or cell, such as interleukin 1α (IL-1α), interleukin-1β (IL-1β), interleukin 6 (IL-6), and tumor necrosis factor (TNF-α). In addition, the anti-inflammatory mediator may be interleukin 1 receptor antagonist (IL-1RA), tumor necrosis factor receptor antagonist (TNF-RA) or derivatives thereof, soluble TNF receptors, or anti-TNF antibodies, for example. Methods according to the invention may involve the step of administering one or more cytokines, chemokines (e.g., interleukin-8 (IL-8)), interferons, or other hormones (e.g., vasoactive intestinal peptide (VIP)).

Although the methods according to the invention may be used to predict, determine, measure or monitor the responsiveness of a subject to any drug that may cause an increase in RNA levels of at least one gene but that does not cause an increase in RNA levels of at least one other gene, the assay is ideally suited for predicting, determining, measuring or monitoring the responsiveness of a subject to steroids.

In a preferred embodiment, differential cytokine-dependent or cytokine-independent transcriptional activities of the steroid responsive and steroid nonresponsive genes in the presence or absence of glucocorticoids is used to measure steroid responsiveness. The preferred genes of interest for measuring steroid responsiveness are derived from the serum amyloid A (SAA) gene superfamily. One SAA gene, serum amyloid A1 (SAA1), is responsive to glucocorticoids both in vivo and in vitro, causing an increase in transcription of SAA1 RNA and a concomitant increase in SAA1 RNA levels. Another SAA gene, serum amyloid A2 (SAA2) is not responsive to glucocorticoids. Thus, a preferred steroid responsive gene according to the invention is SAA1 and a preferred steroid non-responsive gene is SAA2. Alternatively, the steroid responsive gene may encode another acute phase reactant, chemokine, cytokine agonist, cytokine antagonist, complement component, or other gene that is responsive to steroids (i.e., steroid treatment causes an increase in RNA levels). Accordingly, the steroid-non-responsive gene may encode an acute phase reactant, chemokine, cytokine agonist, cytokine antagonist, complement component, or other gene which is not responsive to steroids (i.e., steroid treatment does not cause an increase in RNA levels).

SAA1 transcription, but not SAA2 transcription, is induced in response to steroids in the absence of cytokines in some cell types (e.g., oral epithelial). Other cell types (e.g., HEPG2 hepatoma) require the presence of endogenous (e.g., due to ongoing inflammation), or exogenously administered cytokines, to achieve induction of SAA1 and SAA2 transcription which permits a subsequent or coincident steroid-dependent transcriptional enhancement of the SAA1 but not the SAA2 gene. Cell types which do not require such exposure to endogenous or exogenous cytokines are particularly useful for determining steroid responsiveness in a non-inflamed individual (e.g., a pre-surgery, pre-transplantation, or pretreatment patient).

In another preferred embodiment, the methods according to the invention may be used to evaluate steroid responsiveness in response to the administration of a combination of stimuli or drugs, such as one or more of IL-1, IL-6 and TNF-α and may thereby be useful in evaluating therapies under a range of inflammation conditions and/or treatment modalities. For example, the steroid responsive and non-responsive genes according to the methods of the invention may be chosen depending upon their ability to respond to IL-1 and IL-6, administered separately or in combination, with or without steroids. For example, both the SAA1 gene and SAA2 genes respond to IL-1 strongly and IL-6 weakly, but only the responses of the SAA1 gene are augmented by glucocorticoid administration. By comparison, the C reactive protein gene (CRP) responds weakly to IL-1 and strongly to IL-6, and both responses are augmented by glucocorticoid administration. The SAA genes and the CRP gene are therefore markers for subsets of genes that respond differentially to certain cytokines alone or in combination with steroids and/or other drugs. Thus, a comparison of the RNA levels of the SAA genes and the CRP genes, and/or other genes, may provide useful RNA profiles which predict, determine, measure or monitor a subject's ability to respond to steroids at certain points during an acute phase response (i.e., depending upon the "mix" of cytokines present at that point in time) or to certain cytokines, cytokine antagonists, anti-inflammatory or other drug treatments in the absence of, or in combination with, endogenous or exogenous (i.e., therapeutically administered) steroids.

Methods according to the invention may therefore further include the step of quantifying the RNA level of a third gene, or additional genes, and comparing the RNA level from the third or additional genes to the RNA levels of the steroid responsive gene and the RNA level of the steroid non-responsive gene. In a preferred embodiment, the third gene may encode an acute phase reactant, chemokine, cytokine agonist, cytokine antagonist, or complement component. Exemplary third genes are CRP, complement component 3 (C3), Factor B, or albumin.

Methods according to the invention are preferably used to predict, determine, measure or monitor the steroid responsiveness of a subject who suffers from an inflammatory condition, a disease with an inflammatory component, a disease with an inflammatory consequence, and/or a disease with inflammatory symptoms. The subject may be assayed to determine if he or she will respond to, will not respond to, is refractory to, is less responsive to, or is more responsive to steroid treatment, or is steroid dependent. Methods according to the invention are particularly useful for predicting, determining, measuring or monitoring the steroid responsiveness of a subject who suffers from an arthritic disease such as, for example, osteoarthritis, rheumatoid arthritis, psoriatic arthritis or idiopathic arthritis. Methods according to the invention are also useful for predicting, determining, measuring or monitoring the steroid responsiveness of a subject who suffers from an autoimmune disease, such as an inflammatory bowel disease (e.g., Crohn's disease or ulcerative colitis). Other diseases and conditions that have an inflammatory component or consequence include, but are not limited to, asthma, adult respiratory distress syndrome, systemic lupus erythematosus, multiple sclerosis, insulin-dependent diabetes mellitus, autoimmune arthritis, juvenile rheumatoid arthritis, psoriatic arthritis, inflammatory pulmonary syndrome, pemphigus vulgaris, idiopathic thrombocytopenic purpura, cerebral edema, autoimmune meningitis, myasthenia gravis, autoimmune thyroiditis, sarcoidosis, dermatitis, atopic dermatitis, eczematous dermatitis, psoriasis, Sjogren's Syndrome, sarcoidosis, keratoconjunctivitis sicca secondary to Sjogren's Syndrome, alopecia areata, allergic responses due to arthropod bite reactions, aphthous ulcer, iritis, conjunctivitis, keratoconjunctivitis, cutaneous lupus erythematosus, scleroderma, vaginitis, proctitis, drug eruptions, Stevens-Johnson syndrome, leprosy reversal reactions, erythema nodosum leprosum, autoimmune uveitis, allergic encephalomyelitis, aplastic anemia, pure red cell anemia, autoimmune destruction of erythrocytes, idiopathic thrombocytopenia, polychondritis, Wegener's granulomatosis, chronic active hepatitis, alcohol liver disease, Graves ophthalmopathy, primary biliary cirrhosis, uveitis posterior and interstitial lung fibrosis.

Alternatively, methods according to the invention are used to determine steroid responsiveness in a subject who is being evaluated as a candidate for, is about to undergo, or has undergone a tissue or organ transplant. Alternatively, the subject has cancer, is being treated for cancer, or is in remission for cancer (e.g., solid tumors, acute lymphocytic leukemia and lymphoma). Alternatively, the subject suffers from or the assay is used to diagnose or monitor, a renal disease, allergy, infectious disease, ocular disease, skin disease, gastrointestinal disease, endocrine disease, stroke, coronary artery disease, vascular disease, atherothrombotic disease, spinal cord injury, acute adrenal insufficiency, chronic primary adrenal insufficiency, secondary adrenal insufficiency, and/or congenital adrenal hyperplasia. Alternatively, the subject is being evaluated as a candidate for, is about to undergo, or has undergone steroid replacement or substitution therapy.

In a preferred embodiment of the invention, the steroid responsive gene is controlled by a steroid responsive element, such as a glucocorticoid responsive element (GRE). The GRE may be a consensus GRE or a non-consensus GRE. The consensus GRE is preferably GGTA-CAnnnTGTTCT (SEQ ID NO:1), where n is any nucleotide (A, G, C or T), or a variation thereof. Alternatively, the first gene is controlled either in cis or in trans (e.g., in each case either proximally or distally) by a non-consensus element that permits the gene to respond to steroids. The steroid may provide a signal via the glucocorticoid receptor (GR) or via another steroid (e.g., estrogen, progesterone, etc.) receptor that may engage the GRE and/or another steroid response element in the steroid responsive gene, or at another genomic location. In a preferred embodiment, the steroid non-responsive gene is encoded by a gene which is not controlled by a steroid response element.

The steroid used in the methods according to the invention may be, for example, a glucocorticoid, an estrogen, or an androgen. Exemplary steroids include, but are by no means limited to, alclometasone diproprionate, amcinonide, beclomethasone diproprionate, betamethasone, betamethasone benzoate, betamethasone diproprionate, betamethasone sodium phosphate, betamethasone sodium phosphate and acetate, betamethasone valerate, clobetasol proprionate, clocortolone pivalate, cortisol (hydrocortisone), cortisol (hydrocortisone) acetate, cortisol (hydrocortisone) butyrate, cortisol (hydrocortisone) cypionate, cortisol (hydrocortisone) sodium phosphate, cortisol (hydrocortisone) sodium succinate, cortisol (hydrocortisone) valerate, cortisone acetate, desonide, desoximetasone, dexamethasone, dexamethasone acetate, dexamethasone sodium phosphate, diflorasone diacetate, fludrocortisone acetate, flunisolide, fluocinolone acetonide, fluocinonide, fluorometholone, flurandrenolide, halcinonide, medrysone, methylprednisolone, methylprednisolone acetate, methylprednisolone sodium succinate, mometasone furoate, paramethasone acetate, prednisolone, prednisolone acetate, prednisolone sodium phosphate, prednisolone tebutate, prednisone, triamcinolone, triamcinolone acetonide, triamcinolone diacetate, and triamcinolone hexacetonide or a synthetic analog thereof, or a combination thereof.

The invention further contemplates the administration of one or more steroid inhibitors or steroid antagonists. Exemplary steroid inhibitors include, but are not limited to, mitotane, metyrapone, aminoglutethimide, ketoconazole, and trilostane.

The steroid may be administered any number of ways, including, for example, parenterally, orally, locally, rectally, intravenously, topically, intramuscularly, enterally, transdermally, nasally, ocularly, transmucosally, via inhilation, and/or subcutaneously.

In another aspect, the invention provides a kit for determining drug (e.g., steroid) responsiveness in a subject which has a probe specific for, or primers specific for amplifying, RNA encoded by a drug-responsive gene and probes specific for, or primers specific for amplifying, RNA encoded by a drug non-responsive gene. Preferably, the kit also has a tissue, body fluid or cell collector. In a preferred embodiment, the collector contains RNase inhibitors and other inhibitors and preservatives for minimizing degradation of RNA and DNA. For example, a PAXgene™ Blood RNA tube (Qiagen, Hilden, Germany) may be used.

BRIEF DESCRIPTION OF THE DRAWINGS

The foregoing and other objects, features and advantages of the present invention, as well as the invention itself, will be more fully understood from the following description of preferred embodiments when read together with the accompanying drawings, in which:

FIG. 1 is an alignment of SAA1 and SAA2 promoters. The proximal 450 bases of the human SAA1 and SAA2 promoters (SEQ ID Nos: 2 and 3) were aligned using the ClustalW program. Putative transcription factor binding sites are underlined once (predicted by TESS program), with dots (predicted by Signalscan program) or twice (predicted by visual inspection). Dashes represent gaps in one sequence relative to the other. The Xma1 site is boxed.

FIG. 2 is a timecourse of the induction of SAA1 and SAA2 promoter luciferase reporter constructs in the presence or absence of cytokine and/or dexamethasone treatment. HepG2 cells transfected with pGL2-SAA2pt (A) or pGL2-SAA1pt (B) luciferase reporter constructs were treated with medium only, dexamethasone (50 nM), IL-1 (10 ng/ml), IL-1 plus dexamethasone, IL-6 (10 ng/ml), IL-6 plus dexamethasone, IL-1 plus IL-6, or IL-1 plus IL-6 plus dexamethasone. Cells were harvested 3, 6, 9 and 24 hours after treatment and relative luciferase values were calculated and compared to untreated controls.

SAA1pt or pGL2-SAA2pt were treated with increasing amounts of dexamethasone (10 nM, 50 nM, 100 nM, 500 nM, 1 µM) in the absence or presence of 10 ng/ml IL-1 plus 10 ng/ml IL-6. Cells were harvested 4 hours after treatment and relative luciferase values were calculated and compared to untreated controls.

Figure 4:
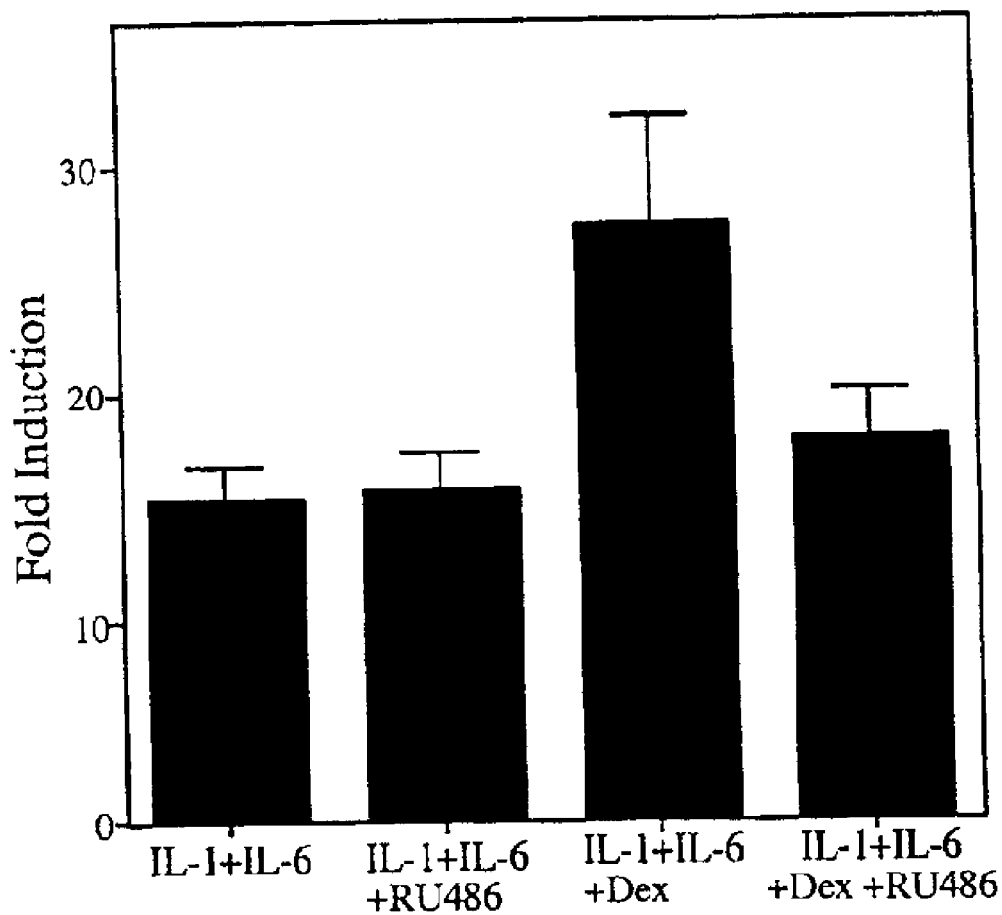

FIG. 4 shows that SAA1 glucocorticoid responsiveness is glucocorticoid receptor (GR) dependent. HepG2 cells were transfected with pGL2-SAA1pt and treated with 10 ng/ml IL-1 plus 10 ng/ml IL-6, alone and in the presence of 10 nM RU486 and/or 100 nM dexamethasone. Cells were harvested 4 hours after treatment and relative luciferase values were calculated and compared to untreated controls.

Figure 5:
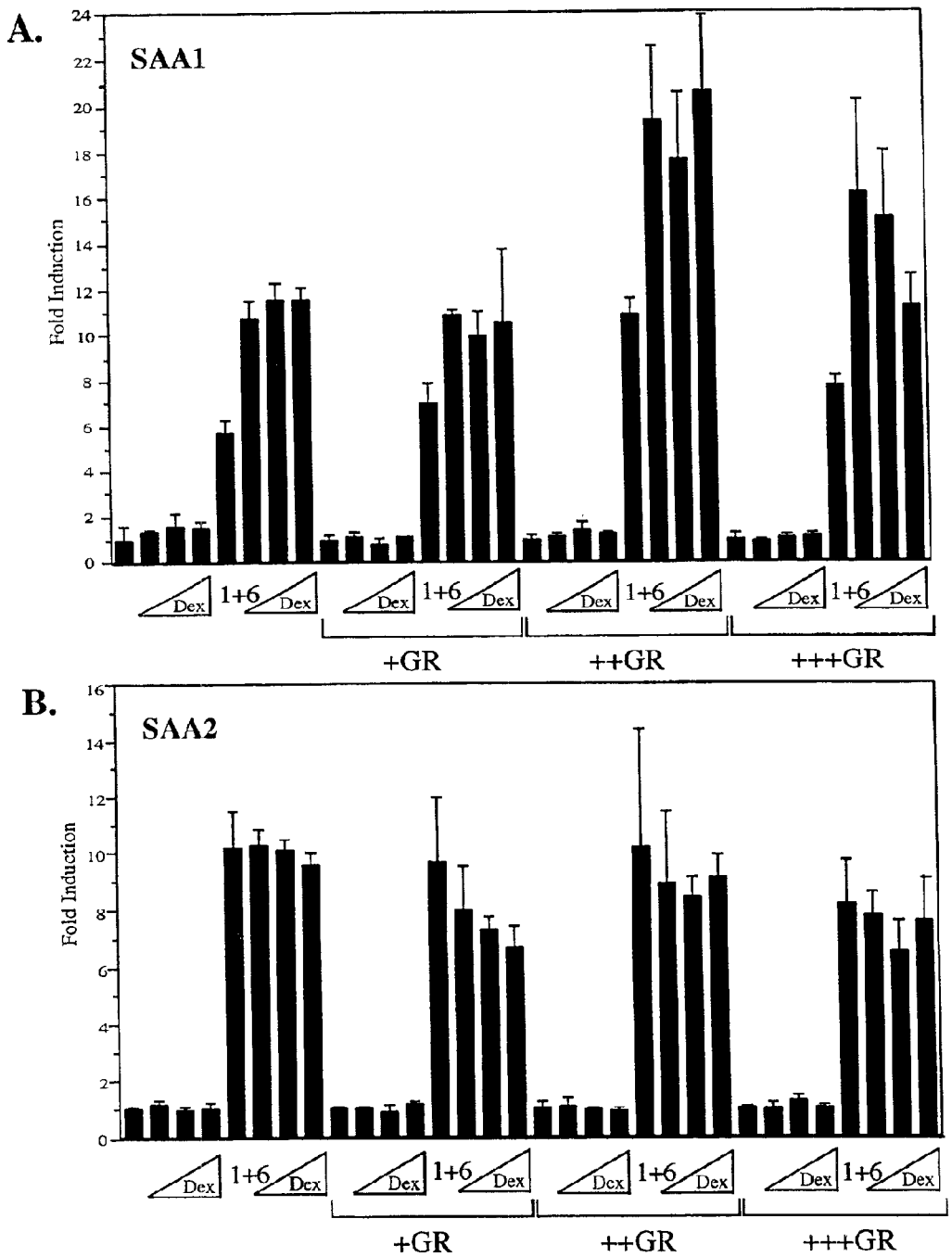

FIG. 5 shows that SAA1 glucocorticoid responsiveness is dependent on cytokine driven transcriptional activation. HepG2 cells co-transfected with the pGL2-SAA1[0.25] (A) or pGL2-SAA2[0.25] (B) and 0, 5, 25 or 50 ng/well CMX-GR expression construct were treated with increasing amounts of dexamethasone (0, 50 nM, 500 nM, 5 µM) in the absence or presence of 10 ng/ml IL-1 plus 10 ng/ml IL-6. Cells were harvested 4 hours after treatment and relative luciferase values were calculated and compared to untreated controls.

Figure 6:
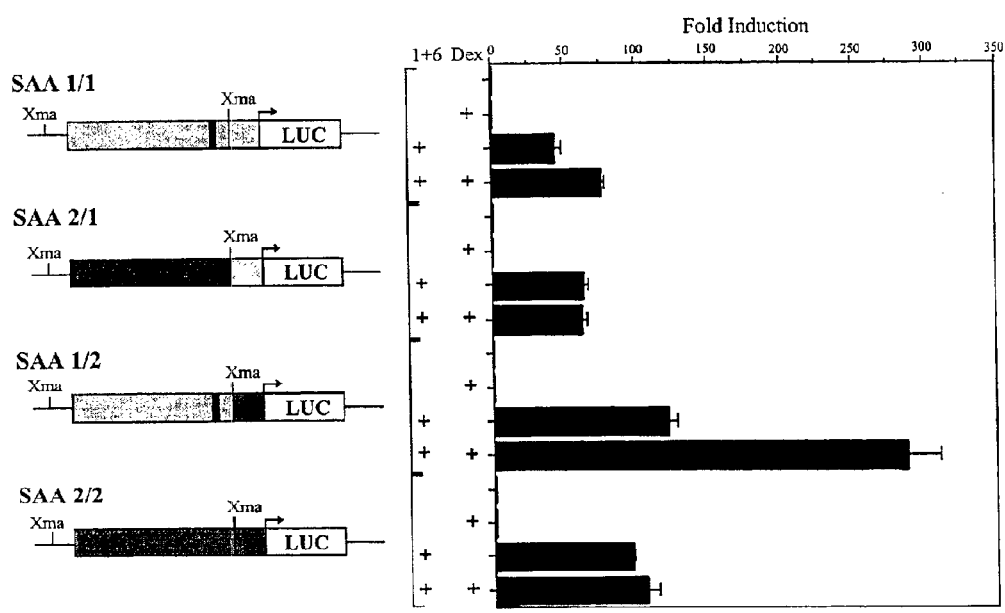

FIG. 6 shows cytokine and dexamethasone induction of chimeric SAA promoters. (A) Schematic diagram of the chimeric SAA promoter constructs. Sequence derived from SAA1 is represented by pale gray shading; sequence derived from SAA2 is represented by dark gray shading; the luciferase coding sequence is represented by "Luc"; the transcription start site is indicated with an arrow. The positions of the Xma 1 restriction enzyme sites used for generating the chimeras are indicated. The putative GRE is represented by a black box. (B) Chimeric constructs were transfected into HepG2 cells and treated with medium only, 50 nM dexamethasone, 10 ng/ml IL-1 plus 10 ng/ml IL-6, or IL-1 plus IL-6 plus dexamethasone. Cells were harvested 4 hours after treatment and relative luciferase values were calculated and compared to untreated controls.

Figure 7:
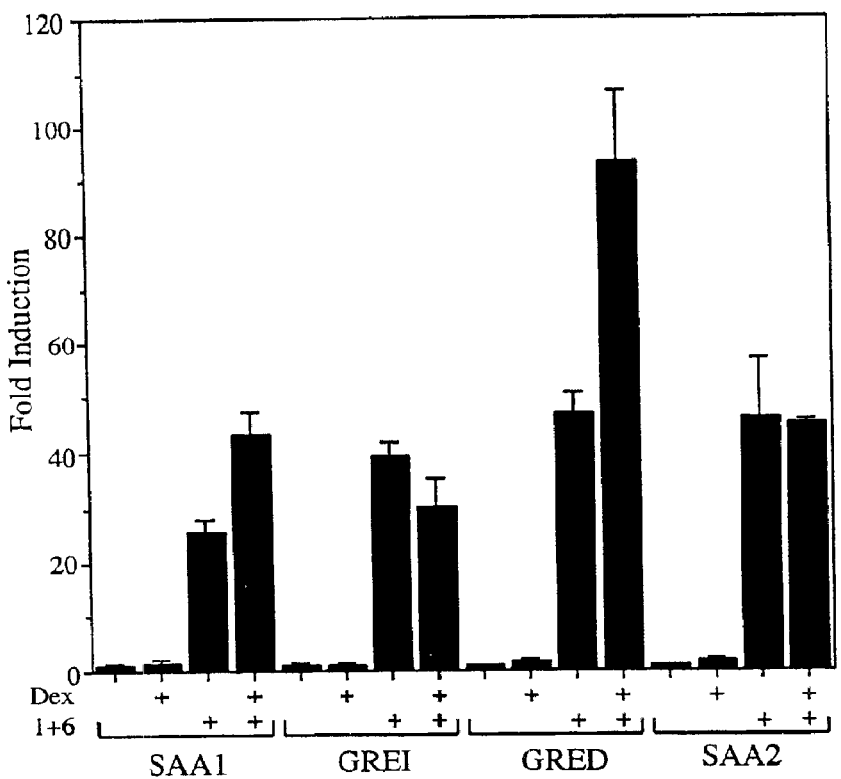

FIG. 7 shows GRE mutant SAA promoters. (A) Alignment of the region of SAA1 encompassing the GRE, the corresponding regions of SAA2, the mutants GREI and GRED and the consensus GRE sequence. (B) HepG2 cells were transfected with pGL2-SAA1[0.7], GREI, GRED or pGL2-SAA2[0.7] constructs and treated with medium only, 50 nM dexamethasone, 10 ng/ml IL-1 plus 10 ng/ml IL-6, or IL-1 plus IL-6 plus dexamethasone. Cells were harvested 4 hours after treatment and relative luciferase values were calculated and compared to untreated controls.

FIG. 8 shows the response of the endogenous human SAA1 and SAA2 genes to cytokines and dexamethasone. (A) Alignment of the 335 bp SAA1 (nucleotides 187 to 273 of SEQ ID NO:4; nucleotides 404 to 520 of SEQ ID NO:5) and 361 bp SAA2 (nucleotides 187 to 273 of SEQ ID NO:6; nucleotides 404 to 546 of SEQ ID NO:6) RT-PCR product sequences. The numbering refers to the full mRNA sequences. The intron exon boundary is marked with a vertical line, amplification from genomic DNA would generate a product that incorporates sequence encompassing the 384 bp (SAA1) or 394 bp (SAA2) intron at this position. The 3' UTRs are underlined once and the primer sequences are underlined twice. Diagonal lines represent 121 bases of aligned sequences which contain no gaps. Dashes represent regions of the SAA2 3'UTR that have no counterpart in the SAA1 3'UTR. (B) HepG2 cells were treated with medium only, 100 nM dexamethasone, 10 ng/ml IL-1 plus 10 ng/ml IL-6 or IL-1 plus IL-6 plus dexamethasone for 24 hours. RNA was extracted, reverse transcribed and amplified as described. PCR products were separated by 8% polyacrylamide gel electrophoresis. This image depicts the relative amounts of SAA1 and SAA2 product within each sample.

DETAILED DESCRIPTION OF THE INVENTION

The invention provides diagnostic assays for measuring the responsiveness of a subject, tissue, body fluid, or cell sample to a drug by comparing the mRNA levels of a gene that responds to the drug, such as a steroid, to the mRNA levels of a gene that does not respond to the drug. Methods according to the invention are useful to predict the ability of a subject (or a tissue, body fluid or cell sample in vitro) to respond to a drug or steroid before and at any stage of treatment, and to monitor the subject over time to assess continued responsiveness to the drug or steroid.

The preferred genes for measuring steroid responsiveness, for example, are serum amyloid A1 (SAA1), which is responsive to glucocorticoids both in vivo and in vitro, and serum amyloid A2 (SAA2), which is not responsive to glucocorticoids. Luciferase reporter constructs carrying the SAA1 and SAA2 promoters were used to demonstrate dose-dependent glucocorticoid enhancement of cytokine driven SAA1 transcription. Using reporter constructs carrying chimeric and mutant SAA promoters, the putative GRE in the SAA1 promoter was confirmed to be functional. SAA1 and SAA2 promoters exhibit qualitatively similar induction profiles in response to cytokines, but the SAA2 promoter had a significant basal and cytokine driven transcriptional advantage (i.e., between 2 and 3 fold) over the SAA1 promoter (see Example 1). The addition of the synthetic glucocorticoid dexamethasone to cytokine treated cells specifically enhanced readout from the SAA1 promoter to a level that is similar to that of the SAA2 promoter. A combination of sequence alignment and in vitro experiments using reporter constructs carrying SAA1/SAA2 promoter chimeras and SAA1 and SAA2 promoters that had been modified by site specific mutagenesis identified a functional glucocorticoid response element (GRE) in the SAA1 promoter only.

An RT-PCR based method was used to distinguish between the products generated by amplification from the SAA1 and SAA2 mRNAs (see Example 2). This method exploits differences in the 3'-untranslated regions (UTRs) of the transcripts, resulting in SAA1 mRNA being 26 residues shorter than SAA2 mRNA. Primers flanking the regions that contribute to this size disparity were used to amplify products of 335 and 361 base pairs (bp) from cDNA generated from the SAA1 and SAA2 mRNAs, respectively. The amplification products were resolved on 8% polyacrylamide gels and quantified by image analysis using NIH Image. Application of this method to total RNA extracted from HepG2 cells yielded results that parallel those obtained with the promoter reporter constructs. The ratio of SAA1 product to SAA2 product was 2:5 following treatment with IL-1 plus IL-6, indicating that the endogenous SAA2 gene has a significant transcriptional advantage (i.e., about 2.5 fold) when induced by cytokines in the absence of glucocorticoids. In contrast, the ratio of SAA1 to SAA2 product, from cells treated with IL-1 plus IL-6 plus dexamethasone was 5:4, indicating a "switch" in transcriptional advantage from SAA2 to SAA1 in the presence of steroids.

In the liver, upregulation of A-SAA protein synthesis during the acute phase response (APR) appears to be a two step process involving an initial cytokine driven phase followed by, or coincident with, a glucocorticoid enhanced cytokine dependent phase. During the first phase, in which the SAA1 and SAA2 promoters are engaged by the transcription factors NF-kappaB and NF-IL6, SAA2 has a significant transcriptional advantage over SAA1. In the second phase only the SAA1 promoter is additionally engaged by the GR, the result of which is to enhance its transcriptional activity to a level similar to that exhibited by the SAA2 promoter in both phases. In cells in which glucocorticoids can upregulate SAA1 transcription, but not SAA2 transcription, in the absence of cytokine stimulation, only the SAA1 promoter is engaged by the GR. Thus, the ratios of SAA1 and SAA2 RNAs and proteins may change over time with a bias strongly in favor of SAA2 in the early APR giving way to increasing relative amounts of SAA1 later. Furthermore, the absolute concentrations of each of the A-SAAs during chronic inflammation may depend on the nature of the underlying disease, and therefore the "mix" of pro- and anti-inflammatory mediators present. The introduction of anti-inflammatory steroid therapy may further modify the ratio of SAA1 and SAA2 mRNA depending on the type and therapeutic dose of synthetic glucocorticoids used.

In a preferred embodiment, RNA levels are quantified by amplification of the RNAs by, for example, reverse transcription polymerase chain reaction (RT-PCR) and resolution/quantification of the reaction products by gel electrophoresis (e.g., slab, capillary, etc.) and product measurement (e.g., by scanning, laser, etc.) or Northern blot analysis of the RNAs. Alternatively, RNA levels are quantified by in situ detection according to standard methods. In a preferred embodiment of the invention, probes capable of hybridizing specifically to SAA1 or SAA2 RNA, are attached to a solid phase support, e.g., a "chip" or "DNA probe array". Oligonucleotides can be bound to a solid support by a variety of processes, including lithography. For example, a chip can hold up to about 250,000 oligonucleotides. The solid phase support is then contacted with a test nucleic acid and hybridization to the specific probes is detected. Accordingly, the quantification of numerous samples (e.g., different tissues from the same individual or samples from different individuals) or the profiling of the RNA levels of a number of steroid or drug responsive or non-responsive genes can be identified in a single hybridization experiment.

In another embodiment, an oligonucleotide ligation assay (OLA) (U.S. Pat. No. 4,998,617) may be used. The OLA protocol uses two oligonucleotides which are designed to be capable of hybridizing to abutting sequences of a single strand of a target. One of the oligonucleotides is linked to a separation marker, e.g,. biotinylated, and the other is detectably labeled. If the precise complementary sequence is found in a target molecule, the oligonucleotides hybridize such that their termini abut, and create a ligation substrate. Ligation then permits the labeled oligonucleotide to be recovered using avidin, or another biotin ligand. Nickerson, D. A. et al. ((1990) *Proc. Natl. Acad. Sci. USA* 87:8923–27) have described a nucleic acid detection assay that combines attributes of PCR and OLA. In this method, PCR is used to achieve the exponential amplification of target DNA, which is then detected using OLA.

Several techniques based on this OLA method have been developed and are useful for detecting RNA. For example, U.S. Pat. No. 5,593,826 discloses an OLA using an oligonucleotide having 3'-amino group and a 5'-phosphorylated oligonucleotide to form a conjugate having a phosphoramidate linkage. In another variation of OLA described in Tobe et al. ((1996), *Nucleic Acids Res.* 24: 3728), OLA combined with PCR may permit the detection and quantification of SAA1 and SAA2 RNAs and other RNAs (e.g., CRP) in a single microtiter well. By marking each of the isoform-specific primers with a unique hapten, i.e., digoxigenin and fluorescein, each OLA reaction can be detected by using hapten specific antibodies that are labeled with different enzyme reporters, alkaline phosphatase or horseradish peroxidase. This system permits the detection of two closely related but distinct isoforms (e.g., SAA1 and SAA2 RNAs) using a high throughput format that leads to the production of two different colors. This system also permits the detection of additional RNAs, such as CRP.

RNA may be quantified from any tissue, body fluid or nucleated cell sample. In a preferred embodiment, the bodily fluid is blood that is obtained by known techniques (e.g., venipuncture). Alternatively, the methods according to the invention can be performed on dry cell samples (e.g., hair or skin) particularly when RT-PCR is used to amplify the RNA. The tissue sample may be derived from a biopsy of any tissue in which the genes of interest (i.e., the drug or steroid responsive gene and the drug or steroid non-responsive gene) are expressed.

Preparations for oral administration of a drug or steroid may be suitably formulated to give controlled release of the active compound. For buccal administration, the drug or steroids may take the form of tablets or lozenges formulated in a conventional manner. Alternatively, an area may be swabbed, sprayed or applied with a steroid or drug prior to obtaining a post-treatment sample (e.g., by scraping). For administration by inhalation, the drug or steroid for use according to the methods of the invention is conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g., gelatin for use in an inhaler or insufflator may be formulated containing a powder mix of the drug or steroid and a suitable powder base such as lactose or starch.

The drugs or steroids may be formulated for parenteral administration by injection, e.g., by bolus injection or continuous infusion. Formulations for injection may be presented in unit dosage form, e.g., in ampoules or in multi-dose containers, with an added preservative. The drugs or steroids may take such forms as suspensions, solutions or emulsions in oily or aqueous vehicles, and may contain formulatory agents such as suspending, stabilizing and/or dispersing agents. Alternatively, the drugs or steroids may be in powder form for constitution with a suitable vehicle, e.g., sterile pyrogen-free water, before use.

The drugs or steroids may also be formulated in rectal drugs or steroids such as suppositories or retention enemas, e.g., containing conventional suppository bases such as cocoa butter or other glycerides.

The drugs or steroids may also be formulated as a depot preparation. For example, parenteral depot systems (PDS) are injected or implanted into the muscle or subcutaneous tissue and incorporated drug released in a controlled manner, allowing the adjustment of release rates over extended periods of time, ranging from several days up to one year. Such long acting formulations may be administered by implantation (e.g., subcutaneously or intramuscularly) or by intramuscular injection. The drugs or steroids may be formulated with suitable polymeric or hydrophobic materials (e.g., as an emulsion in an acceptable oil) or ion exchange resins, or as sparingly soluble derivatives, such as a sparingly soluble salt. Other suitable delivery systems include microspheres which offer the possibility of local noninvasive delivery of drugs over an extended period of time. This technology utilizes microspheres of precapillary size which can be injected via a coronary catheter into any selected part of the body, e.g., the eye, or other organs without causing inflammation or ischemia. The administered drug or steroid is slowly released from these microspheres and taken up by surrounding tissue cells.

Systemic administration of the drug or steroid can also be by transmucosal or transdermal means. For transmucosal or transdermal administration, penetrants appropriate to the barrier to be permeated are used in the formulation. Such penetrants are generally known in the art, and include, e.g., for transmucosal administration bile salts and fusidic acid derivatives. In addition, detergents may be used to facilitate permeation. Transmucosal administration may be through nasal sprays or using suppositories. For topical administration, the oligomers of the invention are formulated into ointments, salves, gels, or creams as generally known in the art. A wash solution may be used locally to treat an injury or inflammation to accelerate healing.

The invention further provides for non-human transgenic animals, which are useful for a variety of purposes, e.g., studying steroid responsiveness in vivo in an animal model, identifying therapeutics for inflammatory diseases or toxicity testing. Transgenic animals of the invention include non-human animals containing a first reporter gene (e.g., green fluorescent protein) under the control of a drug or steroid responsive promoter and a second different reporter gene (e.g., yellow fluorescent protein) under the control of a drug and/or cytokine and/or steroid non-responsive promoter. In a preferred embodiment, a vector containing both reporter transgenes is used to make the transgenic animal. In a preferred embodiment, the human SAA1 and SAA2 gene promoters are used. In one embodiment, the reporter genes are the human SAA1 and SAA2 genes operatively linked to their own promoters, preferably on a single vector construct. Methods according to the invention are then practiced on the transgenic animals or their tissues, body fluids or cells. Such animals are useful for determining or monitoring drug or steroid responsiveness or dosing drugs or steroids in vivo, or studying the side effects of such drugs or steroids in an animal model. Such animals can also be used for studying drugs that are not primarily known to be anti-inflammatory or immune modifying, to establish whether they have an effect on inflammatory or immune processes (e.g., a side effect) for which the SAA1 and SAA2 transgenes provide a readout. An alternative embodiment would follow the above strategy using, for example, the human SAA1 and human CRP gene promoters or the human SAA2 and human CRP gene promoters.

Methods for obtaining transgenic non-human animals are well known in the art. For insertion, the SAA1 reporter and SAA2 reporter constructs are added to the embryonic stem (ES) cells under appropriate conditions for the insertion method chosen, as is known to the skilled artisan. For example, if the ES cells are to be electroporated, the ES cells and constructs are exposed to an electric pulse using an electroporation machine following the manufacturer's guidelines for use. After electroporation, the ES cells are typically allowed to recover under suitable incubation conditions. The cells are then screened for the presence of the SAA1 and SAA2 construct(s). Where more than one construct is to be introduced into the ES cell, each construct can be introduced simultaneously or one at a time. In a preferred embodiment, a single construct having both the SAA1 reporter and the SAA2 reporter (SAA1/SAA2 construct) is used.

After suitable ES cells containing the SAA1/SAA2 construct in the proper location have been identified, the cells can be inserted into an embryo. Insertion may be accomplished in a variety of ways known to the skilled artisan, however a preferred method is by microinjection. For microinjection, about 10–30 cells are collected into a micropipet and injected into embryos that are at the proper stage of development to permit integration of the foreign ES cell containing the SAA1/SAA2 construct into the developing embryo. For instance, the transformed ES cells can be microinjected into blastocytes. The suitable stage of development for the embryo used for insertion of ES cells is very species dependent, however for mice it is about 3.5 days. The embryos are obtained by perfusing the uterus of pregnant females. Suitable methods for accomplishing this are known to the skilled artisan.

While any embryo of the right stage of development is suitable for use, preferred embryos are male. In mice, the preferred embryos also have genes coding for a coat color that is different from the coat color encoded by the ES cell genes. In this way, the offspring can be screened easily for the presence of the SAA1/SAA2 construct by looking for mosaic coat color (indicating that the ES cell was incorporated into the developing embryo). Thus, for example, if the ES cell line carries the genes for white fur, the embryo selected carries the genes for black or brown fur.

After the ES cell has been introduced into the embryo, the embryo may be implanted into the uterus of a pseudopregnant foster mother for gestation. While any foster mother may be used, the foster mother is typically selected for her ability to breed and reproduce well, and for her ability to care for the young. Such foster mothers are typically prepared by mating with vasectomized males of the same species. The stage of the pseudopregnant foster mother is important for successful implantation, and it is species dependent. For mice, this stage is about 2–3 days pseudopregnant.

Offspring that are born to the foster mother may be screened initially for mosaic coat color where the coat color selection strategy (as described above, and in the appended examples) has been employed. In addition, or as an alternative, DNA from tail tissue of the offspring may be screened for the presence of the SAA1/SAA2 construct using Southern blots and/or PCR as described above. Offspring that appear to be mosaics may then be crossed to each other, if they are believed to carry the SAA1/SAA2 construct in their germ line, in order to generate homozygous knockout animals. Homozygotes may be identified by Southern blotting of equivalent amounts of genomic DNA from mice that are the product of this cross, as well as mice that are known heterozygotes and wild type mice.

Other means of identifying and characterizing the SAA1/SAA2 offspring are available. For example, Northern blots are useful for probing the mRNA for the presence or absence of transcripts encoding one or both of the marker genes. In addition, Western blots are useful to assess the level of expression of the marker gene in various tissues of the offspring by probing the Western blot with an antibody against one or both marker proteins, where this gene is expressed. Finally, in situ analysis (such as fixing the cells and labeling with antibody) and/or FACS (fluorescence

EXEMPLIFICATION

Example 1

Differential SAA1 and SAA2 Promoter Engagement in a Series of Unmodified and Modified Promoter Reporter Constructs Transfected into Human HepG2 Hepatoma Cells Using Various Combinations of IL-1, IL-6 and Glucocorticoids SAA Promoter Luciferase Reporter Constructs The pGL2-SAA2pt construct, which contains 1.2 kb of the human SAA2 promoter upstream of a luciferase reporter was generated as follows. A 1196 bp of the promoter region and 22 bp of the first exon of the human acute phase SAA2 gene was amplified by PCR with the introduction of MluI and XhoI restriction sites at the 5' and 3' ends respectively (5' oligonucleotide: 5'AAGAATTCACG CGTCCATGCATGTTGCGGCCGCTTGGCCATCCTT-TACTTCCT-'3' (SEQ ID NO: 8); 3' oligonucleotide: 5'-TTGAATTCCTCGAGCAGGTA-CCATACATATGTAGCTGAGCTGCGGGTCC-3' (SEQ ID NO:9). The PCR product was subsequently cloned into the multiple-cloning site of the pGL2-Basic vector (Promega, Madison, Wis., USA) which is located upstream of a luciferase reporter gene.

The pGL2-SAA1pt construct was generated as follows. The proximal 3.1 kb of genomic sequence upstream of the human SAA1 transcription start site plus the full 37 bases of 5'UTR was amplified by polymerase chain reaction (PCR) from human genomic DNA (Roche Biomolecular) using forward and reverse primers, HSAA1PF (5'-GAATTCACGCGTTT-GGGCAGGGAATATACTTATTTATGGAAG-3') (SEQ ID NO:10) and HSAAPR (5'-GAATT-CCCATGGT GCTGATCTGTGCTGTAGCTGAGCTGCGGG-3') (SEQ ID NO:11), that incorporate Mlu1 and Nco1 restriction sites, respectively. The product was digested with Mlu1 and Nco1 and directionally cloned into a pGL2 vector which had been modified to include an Nco1 site at the start of the luciferase coding sequence and contains the human SAA2 3'UTR (Longley et al. (1999) J. Immunol. 163:4537–45).

Constructs pGL2-SAA1[0.7] and pGL2-SAA1[0.25] containing 704 and 233 bases of promoter sequence respectively, were generated from pGL2-SAA1pt by PCR using the forward primers 5'-GAATTCACG CGTGCGTGATT-ATAGCTCACTGCAGCCTTGACC-3' (SEQ ID NO:12) and 5'-GAATTCACGCGTGGTCT-CCTGCCTG-3' (SEQ ID NO:13) respectively, and the reverse primer HSAAPR.

Constructs pGL2-SAA2[0.7] and pGL2-SAA2[0.25] containing 700 and 239 bases of promoter sequence respectively, were generated from pGL2-SAA2pt by PCR using the forward primers 5'-TATAACGCG TCCTATTTAACGCACCACACTCT-3' (SEQ ID NO:14) and 5'-GAATTCACGCGTGATCTAGCACCTG-3' (SEQ ID NO:15) respectively, and the reverse primer HSAAPR.

Chimeric promoter constructs containing combinations of defined regions of the SAA1 and SAA2 promoters were generated by restriction digest of pGL2-SAA1[0.7] and pGL2-SAA2[0.7] with Xma1 and heterologous ligation of each linearized distal promoter region with the reciprocal linearized proximal promoter region and vector sequence. The chimeric SAA1/2 promoter contains bases −704 to −164 of SAA1 and −159 to −1 of SAA2. The reciprocal SAA2/1 promoter chimera contains bases −700 to −160 of SAA2 and −163 to −1 of SAA1. The control chimera SAA1/1 was generated by re-ligation of bases −704 to −164 of SAA1 and −163 to −1 of SAA1. The control chimera SAA2/2 was generated by re-ligation of bases −700 to −160 of SAA2 and −159 to −1 of SAA2.

The GREI construct was generated by PCR mutagenesis of pGL2-SAA1[0.7] using primers GREIF (5'-CAGCAAACCTCTCTTGTCCC-3') (SEQ ID NO:16) and GREIR (5'-AGAGAGGTTTGCTGTGCCT-3') (SEQ ID NO:17). The GRED construct was generated by PCR mutagenesis of pGL2-SAA2[0.7] using primers GREDF (5'-CAAGGCACATCTTGTTC-CCATAGGT-3') (SEQ ID NO:18) and GREDR (5'-GGAACAAGATGTGCCTTGGCAATG-3') (SEQ ID NO:19). The integrity of all constructs was verified by DNA sequencing.

The renilla transfection control plasmid is described elsewhere (Behre et al. (1999) Biotechniques 26:24–6, 28). The constitutive human Glucocorticoid Receptor-α expression plasmid, CMX-GR, was obtained from Dr. Ron Evans, The Salk Institute, La Jolla, Calif. (Doucas et al. (2000) Proc. Natl. Acad. Sci. USA 97:11893–8).

Cell Culture and Transient Transfection

Human HepG2 hepatoma cells (ATCC) were cultured in DMEM containing 10% FCS, gentamycin, sodium pyruvate and non-essential amino acids (Gibco BRL). Cells were seeded into 24 well plates 24 hours prior to transfection using FuGENE (Roche Biomolecular) as described in Jensen et al. (2000) J. Immunol. 164:5277–86. Cells transfected with SAA promoter luciferase reporter constructs and renilla control plasmid, were incubated for 16 to 20 hours before replacement of culture medium with fresh medium alone or fresh medium containing 10 ng/ml cytokines and/or dexamethasone and/or RU486 (Mifepristone). IL-1 was purchased from Peprotech. IL-6 was obtained from AstraZeneca. Dexamethasone and RU486 were obtained from Sigma.

Luciferase Assays

Cells were harvested at various times post-treatment, washed in PBS and resuspended in Passive Lysis Buffer (Promega, Madison, Wis.). Lysates were assayed for luciferase and renilla activity using the LLR and Stop and Glo reagents (Promega) in a dual injection luminometer (Turner Designs, Sunnyvale, Calif.). Each treatment was carried out in triplicate and the mean ratio of luciferase to renilla activity and standard deviations were calculated. The ratios are expressed relative to untreated controls and are representative of three independent experiments.

RT-PCR

Total RNA was prepared by LiCl Urea extraction (Auffray and Rougeon (1980) Eur. J. Biochem. 107:303-14) from HepG2 cells treated for 24 hours under various experimental conditions. RT-PCR was carried out in a two step process. cDNA was reverse transcribed from 3 µg of total cellular RNA in a 25 µl reaction containing oligo dT primer, Rnasin, RNase inhibitor and Moloney Murine Leukemia Virus Reverse Transcriptase (Promega) at 42° C. for 1 hour. PCR was performed using 2 µl of cDNA product in a 50 µl reaction containing 125 µM primers, 200 µM dNTPs (Pharmacia Amersham, Piscataway, N.J.), 1× PCR buffer, 5 mM $MgCl_2$, and AmpliTaq polymerase (Perkin Elmer-Roche, Indianapolis, Ind.). The forward primer was 5'-CAGACAAATACTTCCATGCT-3' (SEQ ID NO:20); the reverse primer was an equal mix of 5'-TTTTTTCCACCTCTTAAGTATTTATTAGA-3' (SEQ ID NO:21) and 5'-TTTTTTCCA-CCTCTTAAGCATTTATTAGA-3' (SEQ ID NO:22). PCR conditions were as follows: 95° C. for 5 minutes, followed by 25 cycles of 94° C. for 20 seconds, 51° C. for 1 minute, 72° C. for 1 minute, followed by 72° C. for 5 minutes. Products were separated on 8% polyacrylamide gels at 50 v for 24 hours, stained with ethidium bromide and quantified by NIH Image.

Computer Analysis

Transcription factor consensus binding site predictions were made using the Signalscan and TESS programs available from the Center for Bioinformatics at the University of Pennsylvania at http://www.cbil.upenn.edu. Sequence alignments were carried out using the ClustalW program (Thompson et al. (1994) Nucleic Acids Res. 22:4673–4680) available at http://pbil.ibcp.fr/cgibin/npsa_automat.pl?page=/NPSA/npsa_clustalwan.html.

Sequence Alignment of the Proximal Promoters of SAA1 and SAA2

Alignment of 0.7 kB of the SAA1 and SAA2 sequences immediately upstream of their respective transcription start sites, using the ClustalW program, revealed a very high degree of sequence identity (87%) in the proximal ~450 bp, upstream of which the sequences exhibit a markedly decreased level of identity and many regions of non-contiguity. The alignment of the highly conserved proximal promoter regions is depicted in FIG. 1. Within this alignment there are two short non-contiguous regions that each mandate the introduction of a gap of more than one residue into one of the promoter sequences. These "deletions" are in SAA1 relative to positions −207 to −199 in SAA2 and in SAA2 relative to positions −43 to −40 of SAA1. Close visual inspection revealed a putative 15 base pair GRE consensus sequence (GGCACATCTTGTTCC) (SEQ ID NO:23) (Scheidereit et al. (1983) Nature 304:749–52) in SAA1 (from −208 to −194 of SEQ ID NO:1) that encompasses the first of these non-contiguous regions. These residues are also present in SAA2 (within the sequence from −213 and −190 of SEQ ID NO:2) but are disrupted" by 9 residues from −207 to −199 that have no counterparts in the corresponding location in SAA1 (i.e., between SAA1 residues −203 and −202).

Transcriptional Regulation of the SAA1 and SAA2 Promoters In Vitro by Cytokines and Glucocorticoids To establish the extent to which the SAA1 and SAA2 promoters exhibit qualitatively and quantitatively similar responses to cytokines, and to determine whether the putative SAA1 GRE defined above is functionally active, various reporter constructs containing native and modified SAA1 and SAA2 promoters were assayed for their responsiveness to cytokines and glucocorticoids in vitro. HepG2 cells transfected with either of the A-SAA promoter luciferase reporter constructs, pGL2-SAA1pt or pGL2-SAA2pt, were treated with cytokines for 3, 6, 9 and 24 hours. The SAA2 promoter was moderately induced by IL-1 alone or IL-6 alone and synergistically induced by the simultaneous addition of both cytokines (FIG. 2A). IL-1 driven readout increased from 3 to 24 hours, whereas IL-6 driven readout was highest at 3 hours and decreased through 24 hours. The synergistic response to dual treatment with IL-1 plus IL-6 followed a kinetic profile similar to that observed for IL-6 alone. These results were all in accord with data previously reported by us (Uhlar et al. (1997) J. Immunol. Meth. 203:123–30). The SAA1 promoter exhibited transcription induction profiles in response to single and dual cytokine treatments that were qualitatively and kinetically similar to those of the SAA2 promoter (FIG. 2B). However, SAA2 appeared to have a considerable (~2–3 fold) quantitative transcriptional advantage over SAA1 in response to all three cytokine treatments. Treatment of transfected cells with dexamethasone alone had no effect on the SAA1 promoter. However, co-treatment of transfected cells with 50 nM dexamethasone enhanced the cytokine driven induction of the SAA1 promoter approximately two-fold for all treatments at all timepoints (FIG. 2B). In contrast, dexamethasone had no measurable effect on SAA2 promoter activity under any of the assay conditions (FIG. 2A). These data establish that the SAA1 and SAA2 genes respond differentially to glucocorticoids in the context of an ongoing cytokine dependent transcriptional induction.

A construct containing only 235 bases of the SAA1 promoter (pGL2-SAA1[0.25]) retained all of the quantitative, qualitative and kinetic aspects of cytokine responsiveness and glucocorticoid enhancement exhibited by constructs containing 3.1 kb of sequence upstream of the SAA1 transcription start site, suggesting that all of the critical control elements engaged by the most important inflammatory mediators are located in this short region (data not shown).

Figure 3:
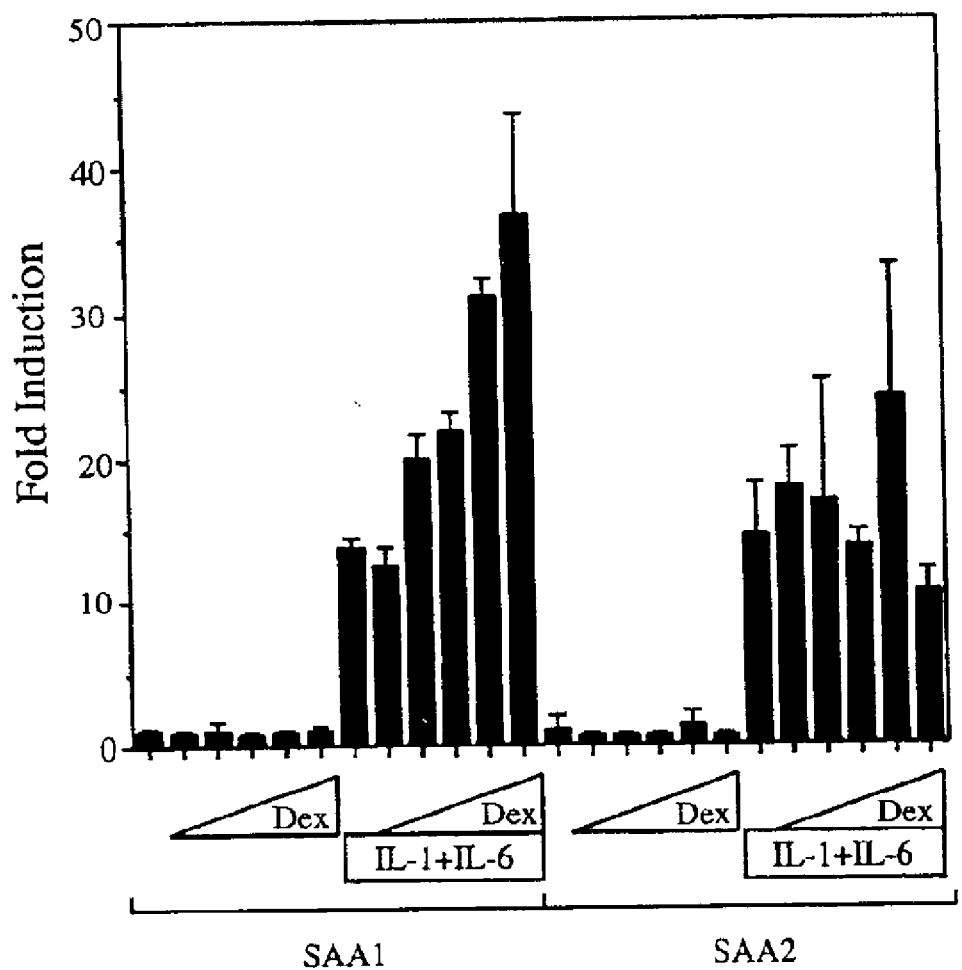
FIG. 3 shows that SAA1 glucocorticoid responsiveness is dose dependent. HepG2 cells transfected with pGL2-

Dose Dependent Glucocorticoid Enhancement of Cytokine Driven SAA1 Promoter Activity To determine whether the non-responsiveness of the SAA1 and SAA2 promoters to dexamethasone alone and of the SAA2 promoter to dexamethasone in the context of cytokine induction was due to sub-optimal dosing, a range of dexamethasone concentrations was assayed. HepG2 cells transfected with either pGL2-SAA1pt or pGL2-SAA2pt were treated with 10 nM, 50 nM, 100 nM, 500 nM or 1 $\mu$M dexamethasone in the presence or absence of IL-1 plus IL-6 for 4 hours (FIG. 3). Neither promoter showed any response to dexamethasone alone, even at the highest dose used. In contrast to the cytokine driven transcriptional readout from the SAA2 promoter, which could not be enhanced by dexamethasone at any concentration, the SAA1 promoter exhibited a clear dose dependent enhancement of transcriptional activity. This suggests that the dexamethasone enhancement of cytokine driven SAA1 promoter activity involves specific receptor mediated events, most likely via glucocorticoid receptors (GRs).

The Enhancement of Cytokine Driven SAA1 Promoter Transcriptional Activity by Glucocorticoids is Glucocorticoid Receptor (GR) Dependent.

To establish that the enhancement of cytokine dependent SAA1 promoter transcriptional activity by glucocorticoids is mediated by the GR, cytokine and dexamethasone treatments similar to those described above were carried out in the presence of the GR antagonist RU486 (Mifepristone). HepG2 cells transfected with pGL2-SAA1pt were treated with IL-1 plus IL-6, in the presence or absence of 100 nM dexamethasone and/or 10 nM RU486 for 4 hours (FIG. 4). The presence of RU486 alone had no measurable effect on the level of cytokine driven SAA1 promoter transcriptional activity. However, RU486 completely blocked the capacity of dexamethasone to quantitatively enhance the induction of the SAA1 promoter by cytokines, limiting the transcriptional readout to that observed in transfected cells treated only with cytokines. This established that the GR is a requisite component in mediating the dexamethasone enhancement of cytokine driven SAA1 transcriptional activity.

The Effect of GR Over-expression on the Capacity of Dexamethasone to Modify SAA1 and SAA2 Gene Transcriptional Activity HepG2 cells have been reported to express only low levels of GR (Baumann et al. (1990) J. Biol. Chem.

265:22275–81). To determine whether the non-response of both promoters to dexamethasone alone, and that of the SAA2 promoter to dexamethasone in the context of cytokine induction, is due to cellular GR levels that are below a functional threshold, SAA1 and SAA2 transcriptional readout was measured in HepG2 cells co-transfected with a constitutive GR expression construct after treatment with various combinations of cytokines and dexamethasone (FIG. 5).

The SAA1 and SAA2 promoters remained non-responsive to dexamethasone alone in HepG2 cells co-transfected with 5, 25 or 50 ng/well of GR expression construct together with pGL2-SAA1pt or pGL2-SAA2pt. However, in the context of cytokine induction of the SAA1 promoter, the dexamethasone enhancement of cytokine driven transcriptional readout could be augmented by co-transfection with the higher amounts (i.e., 25 or 50 ng/well) of GR expression construct (FIG. 5A). These results suggest that the glucocorticoid signaling capacity of native HepG2 cells is not maximized with respect to engagement of the SAA1 promoter GRE. In contrast, co-transfection of GR expression vector could not bring about a dexamethasone dependent enhancement of cytokine driven transcriptional readout from the SAA2 promoter even when cells transfected with the highest levels of GR construct were treated with the highest concentrations of dexamethasone (FIG. 5B). The latter results establish that the SAA2 promoter is truly non-responsive to glucocorticoids.

Chimeric Promoters Containing the Putative SAA1 GRE Retain Glucocorticoid Responsiveness The SAA1 and SAA2 proximal promoter regions each contain Xma1 restriction enzyme sites that are similarly positioned in a highly conserved region immediately downstream of the NF-IL6 site, which itself is immediately downstream of the "GRE" region (FIG. 1). The XmaI site was used to generate chimeras in which the SAA1 and SAA2 "GRE" regions could be reciprocally ligated to the SAA1 and SAA2 proximal promoter regions spanning the approximately 160 bp adjacent to the transcription start site of each gene. The proximal promoter regions are highly conserved (93% identical) and each contain the critically important NfkappaB site in addition to a putative site (between −110 and −102 of SAA1 and −106 and −98 of SAA2) for the transcriptional repressor YY-1; the major difference is a "deletion" in the SAA2 promoter of four residues that are present in the SAA1 promoter between residues −44 and −39 (FIG. 1). The experiments outlined above established that all of the major cytokine and glucocorticoid response elements, together with the promoter feature that confers an apparent baseline and cytokine responsive transcriptional advantage to the SAA2 gene are located within 250 bases of the transcription start site. The chimeric constructs were used to determine the locations of the elements that mandate qualitative and quantitative transcriptional differences between the SAA1 and SAA2 genes relative to the Xma1 site.

Constructs SAA1/1 and SAA2/1, each of which contain the proximal 163 bp of the SAA1 promoter region, exhibited basal and cytokine driven levels of transcriptional activity that are characteristic of the unmodified SAA1 promoter (FIG. 6). Similarly, constructs SAA1/2 and SAA2/2, each of which contain the proximal 159 bp of the SAA2 promoter region, had basal and cytokine driven levels of transcriptional activity that are characteristic of the unmodified SAA2 promoter. Taken together, these experiments suggest that quantitative differences in both the basal and cytokine-driven transcriptional regulation of the SAA1 and SAA2 genes are mandated by minor sequence differences between the respective promoters in the region downstream of the Xma1 site. Constructs SAA1/1 and SAA1/2, which contain the distal region of the SAA1 promoter (i.e., upstream of the Xma1 site) including the putative GRE, were each responsive to dexamethasone in the presence of cytokines. Constructs SAA2/1 and SAA2/2 contain the distal region of the SAA2 promoter and were each non-responsive to dexamethasone. These data strongly suggest that a genetic element in the region between bases −704 and −164 of the SAA1 promoter, most likely the sequence between −208 and −194 that conforms to the GRE consensus, confers the property of glucocorticoid modifiable transcriptional activity to the SAA1 gene.

Confirmation that the Putative GRE in SAA1 is Functional

Site directed mutagenesis experiments were performed to determine whether the putative SAA1 GRE is functional and to exclude the possibility that subtle differences in genomic context, rather than intrinsic sequence differences in the putative SAA1 GRE and SAA2 "disrupted GRE", mandate the differential dexamethasone responsiveness of the genes (and chimeric derivatives thereof). Two modified constructs were generated: the GREI construct contains an SAA1 promoter with a 9 residue sequence (GCAAACCTC) (Nucleotides −207 to −199 of SEQ ID NO:2) inserted into the GRE to form an "SAA2-like disrupted GRE"; the GRED construct contains an SAA2 promoter in which the same 9 residues have been deleted to form an "SAA1-like GRE" (FIG. 7A). The GREI and GRED constructs each retained the basal and cytokine driven levels of transcriptional activity that are characteristic of the unmodified parental promoters from which they were derived. However, the GREI construct had "lost" the capacity to respond to dexamethasone in the presence of cytokines, whereas the GRED construct had "gained" this property (FIG. 7B), thereby establishing that the SAA1 GRE is functional and is both necessary and sufficient to confer glucocorticoid responsiveness in the context of cytokine stimulation.

Example 2

Use of the RT-PCR Assay to Establish that the Ratio of SAA1 and SAA2 Products in HepG2 cells Treated with IL-1 Plus IL-6 Changes According to Whether Glucocorticoid is Present, in a Manner Analogous to that Defined in Promoter-reporter Studies To determine whether the results obtained using the SAA1 and SAA2 promoter luciferase reporter constructs accurately reflect the regulation of the endogenous genes with respect to cytokines and glucocorticoids, an RT-PCR method was developed whereby the relative proportions of the transcription products of each gene could be directly compared. The SAA1 and SAA2 mRNAs, although highly similar (91% identical overall), differ significantly in the central region of their 3'UTRs; the SAA1 mRNA 3'UTR relative to that of the SAA2 mRNA 3'UTR has four "deletions" totaling 26 residues (FIG. 8A).

Forward and reverse PCR primers were designed, each of which can bind cDNA derived from either A-SAA mRNA (FIG. 8A). RT-PCR using these primers generates bands of 335 and 361 base pairs corresponding to products generated from the SAA1 and SAA2 mRNAs respectively. In addition, the primers span intron 3 of each gene, thereby permitting products of amplification from contaminating genomic DNA to be identified. The ratio of 335 bp to 361 bp products, as determined by image analysis following resolution on 8% polyacrylamide gels reflects the relative concentrations of cellular SAA1 and SAA2 mRNAs and serves as a surrogate measure or readout of the transcriptional activation of the SAA1 and SAA2 promoters.

The above RT-PCR method was applied to total RNA from untreated and treated HepG2 cells. Products derived from SAA1 or SAA2 mRNA were not detected in untreated cells or following treatment with dexamethasone alone (FIG. 8B, lanes 1 and 2). However, the ratio of the levels of the SAA1 to SAA2 PCR products was approximately 2:5 following treatment with IL-1 and IL-6 (FIG. 8B, lane 3), indicating that the endogenous SAA2 gene has a significant transcriptional advantage (i.e., ~2.5 fold) when induced by cytokines in the absence of glucocorticoids. In contrast, the ratio of the levels of the SAA1 to SAA2 PCR products from cells treated with IL-1 and IL-6 plus dexamethasone was 5:4 (FIG. 8B, lane 4), indicating that the above cytokine driven transcriptional advantage of the SAA2 promoter is superceded by a modest SAA1 transcriptional advantage in the presence of glucocorticoids. Thus, the responses of the endogenous genes to different combinations of pro-inflammatory mediators paralleled those observed in experiments using isolated promoters to drive a quantifiable reporter, thereby establishing that the SAA1 GRE is functional when in its native genomic and cellular environment.

Example 3

Evaluation of the Glucocorticoid-dependent Differential Transcriptional Activities of the SAA1 and SAA2 Genes for Use in Determining Steroid Responsiveness in Patients with Diseases that Have an Inflammatory Component Inflammatory bowel diseases (IBDs) (e.g., Crohn's and ulcerative colitis) are often treated with steroids, the efficacy of which is variable, both ab initio and over time. The assay according to the invention, which is based on the ratio of SAA1 to SAA2 mRNAs, is a useful tool for predicting and/or assessing steroid responder status. The assay is used to determine whether subjects suffering from IBD, for example, fall into four general categories: (i) in remission (not currently taking steroids but may have taken steroids in the past; (ii) steroid refractory (still with active disease, despite at least four weeks of steroid treatment); (iii) steroid dependent (quiescent on high doses of steroids, but tending to flare up if steroids are withdrawn); or (iv) active disease (naïve with respect to steroid therapy or not having taken steroids for at least six months (e.g., due to previous lack of efficacy and/or side effects).

After informed consent has been given, patients' disease status is evaluated and a 10 ml blood sample and buccal swab (e.g., obtained by gently rubbing the inside of the cheek with a small brush) is obtained. Alternatively, a biopsy sample may be obtained according to standard methods. The blood sample may be taken according to methods known in the art, e.g., in a standard heparin or EDTA blood collection tube or a blood tube which is specially treated or supplemented with an RNA preservative solution that inhibits RNase activity or the like (e.g., a PAXgene™ Blood RNA Tube, Qiagen, Hilden, Germany). The buccal swab is taken using, for example, a CYTO-PAK CytoSoft™ brush (Medical Packages Corp., Camarillo, Calif.) and is placed on ice to avoid degradation of the mRNA, or into an RNA preservative solution to inhibit RNase activity or the like.

Proportional RT-PCR analysis to determine the ratio of SAA1 mRNA to SAA2 mRNA is then performed according to the method of Example 2. Data is analyzed to establish the extent to which particular SAA1:SAA2 ratios are associated with particular steroid response phenotypes. The assay may form the basis of a patient care strategy wherein the ratio of SAA1 mRNA to SAA2 mRNA in nucleated blood cells and/or buccal cells and/or biopsy sample and/or tissue sample is correlated with (i) current clinical response to steroid therapy, and/or (ii) past clinical response to steroid therapy, and/or (iii) future clinical response to steroid therapy.

Equivalents

The invention may be embodied in other specific forms without departing from the spirit or essential characteristics thereof. The foregoing embodiments are therefore to be considered in all respects illustrative rather than limiting of the invention described herein.

I claim:

1. A method for determining steroid responsiveness in a subject, the method comprising the steps of:
   - (a) determining a first level of expression of RNA from a first gene known or suspected to be steroid responsive in a tissue, body fluid or cell from a subject undergoing steroid treatment;
   - (b) determining a second level of expression of RNA from a second gene known or suspected to be non-responsive to steroids in the tissue, body fluid or cell; and
   - (c) comparing the first and second levels of RNA to create a ratio;
   - (d) determining the steroid responsiveness of the subject based on the ratio, wherein the subject is steroid responsive if the ratio is higher than a predetermined control ratio for untreated or nonresponsive subjects, or similar to prior ratios for the subject when the subject was previously determined to be responsive.

2. A method for determining steroid responsiveness in a tissue, body fluid or cell, the method comprising the steps of:
   - (a) exposing a tissue, body fluid or cell sample in vitro to a steroid;
   - (b) determining a first level of expression of RNA from a first gene known or suspected to be steroid responsive;
   - (c) determining a second level of expression of RNA from a second gene known or suspected to be non-responsive to steroids; end
   - (d) comparing the first and second levels of RNA to create a ratio;
   - (e) determining the steroid responsiveness of the tissue, body fluid or cell based on the ratio, wherein the tissue, body fluid or cell sample is steroid responsive if the ratio is higher than a predetermined control ratio for untreated or nonresponsive subjects, or similar to prior ratios for the subject when the subject was previously determined to be responsive.

3. A method for determining steroid responsiveness in a subject, the method comprising the steps of:
   - (a) determining a level of expression of an RNA from a first gene known or suspected to be responsive to steroids in a pre-treatment tissue, body fluid, or cell from a subject;
   - (b) determining a level of expression of an RNA from a second gene known or suspected to be un-responsive to steroids in the pre-treatment tissue, body fluid, or cell;
   - (c) determining a post-treatment level of RNA expressed from the first gene;
   - (d) determining a post-treatment level of RNA expressed from the second gene;
   - (e) comparing the pre-treatment level of RNA expressed from the first gene to the pre-treatment level of RNA expressed from the second gene to create a first normalized value;

(f) comparing the post-treatment level of RNA expressed from the first gene to the post-treatment level of RNA expressed from the second gene to create a second normalized value;

(g) comparing the first normalized value to the second normalized value;

(h) determining steroid responsiveness of the subject based upon the comparison of the first normalized value to the second normalized value, wherein if the first normalized value is less than the second normalized value, it is indicative of steroid responsiveness in the tissue, body fluid or cell, and/or if the first normalized value is greater than or the same as the second normalized value, it is indicative of steroid non-responsiveness in the cell, and/or wherein the difference between the first normalized value and the second normalized value correlates to the ability of the subject to respond to the steroid.

4. A method for determining an effective dose of a steroid in a subject, the method comprising the steps of:

(a) administering to a subject a dose of a steroid;

(b) determining a first level of expression of RNA from a first gene known or suspected to be steroid responsive in a tissue, body fluid, or cell from the subject;

(c) determining a second level of expression of RNA from a second gene known or suspected to be non-responsive to steroids in the tissue, body fluid, or cell; and (d) comparing the first and second levels of RNA to create a ratio;

(e) determining the effective dose of the steroid in the subject based on the ratio, wherein the difference between the first RNA level and the second RNA level is indicative of the effectiveness of the steroid dose in the subject.

5. A method for monitoring a subject's ability to respond to a steroid, the method comprising the steps of:

(a) administering to a subject a dose of steroid;

(b) determining a first level of expression of RNA from a first gene known or suspected to be steroid responsive in a tissue, body fluid, or cell from the subject;

(c) determining a second level of expression of RNA from a second gene known or suspected to be non-responsive to steroids in the tissue, body fluid, or cell; and (d) comparing the first and second levels of RNA to create a ratio;

(e) monitoring the subject's ability to respond to the steroid based upon the ratio, wherein the subject is steroid responsive if the ratio is higher than a predetermined control ratio for untreated or nonresponsive subjects, or similar to prior ratios for the subject when the subject was previously determined to be responsive.

6. A method for determining drug responsiveness in a subject undergoing drug treatment, the method comprising the steps of:

(a) determining a first level of expression of RNA from a first gene known or suspected to be drug-responsive in a tissue, body fluid, or cell from a subject undergoing treatment with a drug;

(b) determining a second level of expression of RNA from a second gene known or suspected to be non-responsive to the drug in the tissue, body fluid, or cell; and (c) comparing the first and second levels of RNA to create a ratio;

(d) determining drug responsiveness in the subject undergoing drug treatment based upon the ratio, wherein the subject is drug-responsive if the first level is higher than the second level and the subject is non-responsive to drug if the second level is higher than the first level.

7. A method for determining drug responsiveness in a tissue, body fluid or cell, the method comprising the steps of:

(a) exposing a tissue, body fluid or cell in vitro to a drug;

(b) determining a first level of expression of RNA from a first gene known or suspected to be drug-responsive;

(c) determining a second level of expression of RNA from a second gene known or suspected to be non-responsive to the drug; and (d) comparing the first and second levels of RNA to create a ratio;

(e) determining drug responsiveness in the tissue, body fluid, or cell based upon the ratio, wherein the tissue, body fluid or cell is drug-responsive if the first level is higher than the second level and the tissue, body fluid or cell is non-responsive to the drug if the second level is higher than the first level.

8. The method of claim 1, wherein one or more of the determining steps requires amplification of the RNAs.

9. The method of claim 8, wherein one or more of the determining steps requires polymerase chain reaction (PCR) of the RNAs.

10. The method of claim 1, wherein one or more of the determining steps requires in situ detection of the first and second RNA.

11. The method of claim 1, wherein one or more of the determining steps requires direct probing of the RNAs.

12. The method of claim 1, further comprising monitoring or tracking steroid responsiveness over time to detect a change in steroid responsiveness.

13. The method of claim 1, further comprising the step of administering one or more pro-inflammatory and/or anti-inflammatory mediators to the tissue, body fluid or cell.

14. The method of claim 13, wherein the pro-inflammatory mediator is selected from the group consisting of interleukin 1α (IL-1α), interleukin-1β (IL-1β), interleukin 6 (IL-6), and tumor necrosis factor (TNF-α).

15. The method of claim 13, wherein the anti-inflammatory mediator is selected from the group consisting of interleukin 1 receptor antagonist (IL-1RA), tumor necrosis factor receptor antagonist (TNF-RA) or derivatives thereof, soluble TNF receptors, anti-TNF antibodies, and anti-TNF-RA antibodies.

16. The method of claim 1, further comprising the step of administering one or more cytokines, chemokines, interferons or hormones to the tissue, body fluid or cell.

17. The method of claim 16, wherein the chemokine is selected from the group consisting of interleukin-8 (IL-8).

18. The method of claim 16, wherein the peptide hormone is selected from the group consisting of vasoactive intestinal peptide (VIP).

19. The method of claim 1, wherein the tissue comprises blood.

20. The method of claim 1, wherein the tissue comprises nucleated cells.

21. The method of claim 1, wherein the cell is selected from the group consisting of a monocyte, a macrophage, a neutrophil, a T-cell, B-cell, a basophil, a fibroblast, an endothelial cell and a epithelial cell.

22. The method of claim 1, wherein the tissue comprises buccal cells.

23. The method of claim 1, wherein the tissue comprises a biopsy sample.

24. The method of claim 1, wherein the tissue sample is stored in a stabilization solution prior to analysis.

25. The method of claim 1, wherein the tissue sample is stored frozen.

26. The method of claim 1, wherein the first gene encodes serum amyloid A1 (SAA1).

27. The method of claim 1, wherein the second gene encodes serum amyloid A2 (SAA2).

28. The method of claim 1, wherein the first gene or second gene encodes a chemokine, a cytokine agonist, a cytokine antagonist, or a complement component.

29. The method of claim 1, further comprising the step of quantifying the RNA level of a third gene and comparing the RNA level from the third gene to the RNA level from the first gene and the RNA level from the second gene.

30. The method of claim 29, wherein the third gene encodes an acute phase reactant.

31. The method of claim 29, wherein the third gene encodes a chemokines, cytokine agonist, a cytokine antagonist, or a complement component.

32. The method of claim 29, wherein the third gene is selected from the group consisting of C-reactive Protein (CRP), complement component 3 (C3), Factor B, and albumin.

33. The method of claim 1, wherein the subject suffers from an inflammatory condition, a disease with an inflammatory component, a disease with an inflammatory consequence, and/or a disease with inflammatory symptoms.

34. The method of claim 1, wherein the subject is being evaluated as a candidate for, is about to undergo, or has undergone a tissue or organ transplant.

35. The method of claim 1, wherein the subject may be refractory, less responsive, or more responsive to steroid treatment.

36. The method of claim 1, wherein the subject has cancer, is being treated for cancer, or is in remission for cancer.

37. The method of claim 1, wherein the cancer is selected from the group consisting of solid tumors, acute lymphocytic leukemia and lymphoma.

38. The method of claim 1, wherein the subject is steroid dependent.

39. The method of claim 1, wherein the subject suffers from an arthritic disease.

40. The method of claim 39, wherein the arthritic disease is selected from the group consisting of osteoarthritis, rheumatoid arthritis, psoriatic arthritis and idiopathic arthritis.

41. The method of claim 1, wherein the subject suffers from an autoimmune disease.

42. The method of claim 1, wherein the subject suffers from an inflammatory bowel disease.

43. The method of claim 42, wherein the subject suffers from Crohn's disease or ulcerative colitis.

44. The method of claim 1, wherein the subject suffers from asthma, adult respiratory distress syndrome, systemic lupus erythematosus, inflammatory bowel disease, Crohn's disease, ulcerative colitis, multiple sclerosis, insulin-dependent diabetes mellitus, autoimmune arthritis, rheumatoid arthritis, juvenile rheumatoid arthritis, psoriatic arthritis, inflammatory pulmonary syndrome, pemphigus vulgaris, idiopathic thrombocytopenic purpura, cerebral edema, autoimmune meningitis, myasthenia gravis, autoimmune thyroiditis, sarcoidosis, dermatitis, atopic dermatitis, eczematous dermatitis, psoriasis, Sjogren's Syndrome, sarcoidosis, keratoconjunctivitis sicca secondary to Sjogren's Syndrome, alopecia areata, allergic responses due to arthropod bite reactions, aphthous ulcer, iritis, conjunctivitis, keratoconjunctivitis, cutaneous lupus erythematosus, scleroderma, vaginitis, proctitis, drug eruptions, Stevens-Johnson syndrome, leprosy reversal reactions, erythema nodosum leprosum, autoimmune uveitis, allergic encephalomyelitis, aplastic anemia, pure red cell anemia, autoimmune destruction of erythrocytes, idiopathic thrombocytopenia, polychondritis, Wegener's granulomatosis, chronic active hepatitis, alcohol liver disease, Graves ophthalmopathy, primary biliary cirrhosis, uveitis posterior and interstitial lung fibrosis or a combination thereof.

45. The method of claim 1, wherein the subject suffers from a renal, allergic, infectious, ocular, skin, gastrointestinal, and/or endocrine disease.

46. The method of claim 1, wherein the subject suffers from stroke, coronary artery disease, vascular disease, atherothrombotic disease and/or spinal cord injury.

47. The method of claim 1, wherein the subject suffers from an endocrine disease.

48. The method of claim 1, wherein the subject is being evaluated as a candidate for, is about to undergo, or has undergone steroid replacement or substitution therapy.

49. The method of claim 1, wherein the subject suffers from acute adrenal insufficiency, chronic primary adrenal insufficiency, secondary adrenal insufficiency, and/or congenital adrenal hyperplasia.

50. The method of claim 1, wherein the first gene is controlled by a steroid responsive element.

51. The method of claim 50, wherein the steroid responsive element is a glucocorticoid responsive element (GRE).

52. The method of claim 51, wherein the GRE is a consensus GRE or a non-consensus GRE.

53. The method of claim 52, wherein the consensus GRE is GGTACAnnnTGTTCT or a variation thereof, where n is any nucleotide.

54. The method of claim 1, wherein the second gene is encoded by a gene which is not controlled by a steroid response element.

55. The method of claim 1, wherein the steroid is selected from the group consisting of a glucocorticoid, an estrogen, and an androgen.

56. The method of claim 1, further comprising the step of administering one or more glucocorticoid inhibitors, glucocorticoid antagonists or other steroid inhibitors or steroid antagonists.

57. The method of claim 56, wherein the glucocorticoid inhibitor is selected from the group consisting of mitotane, metyrapone, aminoglutethimide, ketoconazole, and trilostane.

58. The method of claim 1, wherein the steroid is selected from the group consisting of alclometasone diproprionate, amcinonide, beclomethasone diproprionate, betamethasone, betamethasone benzoate, betamethasone diproprionate, betamethasone sodium phosphate, betamethasone sodium phosphate and acetate, betamethasone valerate, clobetasol proprionate, clocortolone pivalate, cortisol (hydrocortisone), cortisol (hydrocortisone) acetate, cortisol (hydrocortisone) butyrate, cortisol (hydrocortisone) cypionate, cortisol (hydrocortisone) sodium phosphate, cortisol (hydrocortisone) sodium succinate, cortisol (hydrocortisone) valerate, cortisone acetate, desonide, desoximetasone, dexamethasone, dexamethasone acetate, dexamethasone sodium phosphate, diflorasone diacetate, fludrocortisone acetate, flunisolide, fluocinolone acetonide, flucinonide, fluorometholone, flurandrenolide, halcinonide, medrysone, methylprednisolone, methylprednisolone acetate, methylprednisolone sodium succinate, mometasone furoate, paramethasone acetate, prednisolone, prednisolone acetate, prednisolone sodium phosphate, prednisolone tebutate, prednisone, triamcinolone, triamcinolone acetonide, triamcinolone diacetate, and triamcinolone hexacetonide, or a synthetic analog thereof, or a combination thereof.

59. The method of claim 1, wherein the steroid is administered parenterally, orally or locally.

60. The method of claim 1, wherein the steroid is administered intravenously, intramuscularly, enterally, transdermally, nasally, transmucosally, via inhalation, and/or subcutaneously.

* * * * *